US007572231B2

(12) United States Patent
Pearlman

(10) Patent No.: US 7,572,231 B2
(45) Date of Patent: Aug. 11, 2009

(54) METHOD OF AND SYSTEM FOR SIGNAL SEPARATION DURING MULTIVARIATE PHYSIOLOGICAL MONITORING

(76) Inventor: Justin D. Pearlman, 43 Berrill Farms, Hanover, NH (US) 03755

( * ) Notice: Subject to any disclaimer, the term of this patent is extended or adjusted under 35 U.S.C. 154(b) by 706 days.

(21) Appl. No.: 11/020,927

(22) Filed: Dec. 23, 2004

(65) Prior Publication Data

US 2005/0197586 A1 Sep. 8, 2005

Related U.S. Application Data

(63) Continuation-in-part of application No. 09/773,167, filed on Jan. 31, 2001, now abandoned.

(60) Provisional application No. 60/179,192, filed on Jan. 31, 2000.

(51) Int. Cl.
*A61B 5/0402* (2006.01)

(52) U.S. Cl. .................................................. 600/508

(58) Field of Classification Search ................ 600/508, 600/509, 513
See application file for complete search history.

(56) References Cited

U.S. PATENT DOCUMENTS

| | | | |
|---|---|---|---|
| 3,602,215 A | 8/1971 | Parnell | 128/2.06 B |
| 4,094,310 A | 6/1978 | McEachern et al. | 600/525 |
| 4,141,351 A | 2/1979 | James et al. | 128/2.06 R |
| 4,577,639 A | 3/1986 | Simon et al. | 128/709 |
| 4,791,936 A | 12/1988 | Snell et al. | 600/510 |
| 4,887,609 A | 12/1989 | Cole, Jr. | 128/696 |
| 4,991,580 A | 2/1991 | Moore | 128/696 |
| 5,020,540 A | 6/1991 | Chamoun | 128/696 |
| 5,042,498 A | 8/1991 | Dukes | 128/696 |
| 5,209,237 A * | 5/1993 | Rosenthal | 600/511 |
| 5,217,010 A | 6/1993 | Tsitlik et al. | 128/419 PG |
| 5,447,164 A | 9/1995 | Shaya et al. | 600/523 |
| 5,483,968 A | 1/1996 | Adam et al. | 128/696 |
| 5,496,858 A | 3/1996 | Eggensperger et al. | 514/693 |
| 5,511,553 A | 4/1996 | Segalowitz | 128/696 |
| 5,782,238 A | 7/1998 | Beitler | 128/639 |
| 5,817,027 A | 10/1998 | Arand et al. | 600/515 |
| 5,819,741 A | 10/1998 | Karlsson et al. | 600/523 |
| 5,947,897 A | 9/1999 | Otake | 600/372 |
| 5,987,348 A | 11/1999 | Fischer et al. | 600/413 |
| 6,424,960 B1 * | 7/2002 | Lee et al. | 600/515 |

* cited by examiner

*Primary Examiner*—George R Evanisko
(74) *Attorney, Agent, or Firm*—Burns & Levinson LLP; Jacob N. Erlich; Kathleen Chapman

(57) ABSTRACT

Multiple electrode contacts make electrical connections to the anterior and/or posterior chest for multivariate characterization of the electrical activation of the heart. A central processing unit derives synthetic composite electrographic signals as well as flag signals for specific purposes. A preferred embodiment uses this system to trigger or gate magnetic resonance imaging, eliminating or reducing problems from small or inverted R-waves, lead detachment, noise, flow signal, gradient changes, and rhythm changes, more reliably flagging the onset of electrical activation of the ventricles. Additional derived data are ST-segment shifts, filling times, and respiratory cycle. Filling times may be used for greatly improved imaging in the presence of rhythm disturbances, such as atrial fibrillation. Respiratory cycle may be used as a respiratory trigger to control for the effects of breathing on the heart position and image quality.

18 Claims, 16 Drawing Sheets

Figure 9: Chest lead placement example
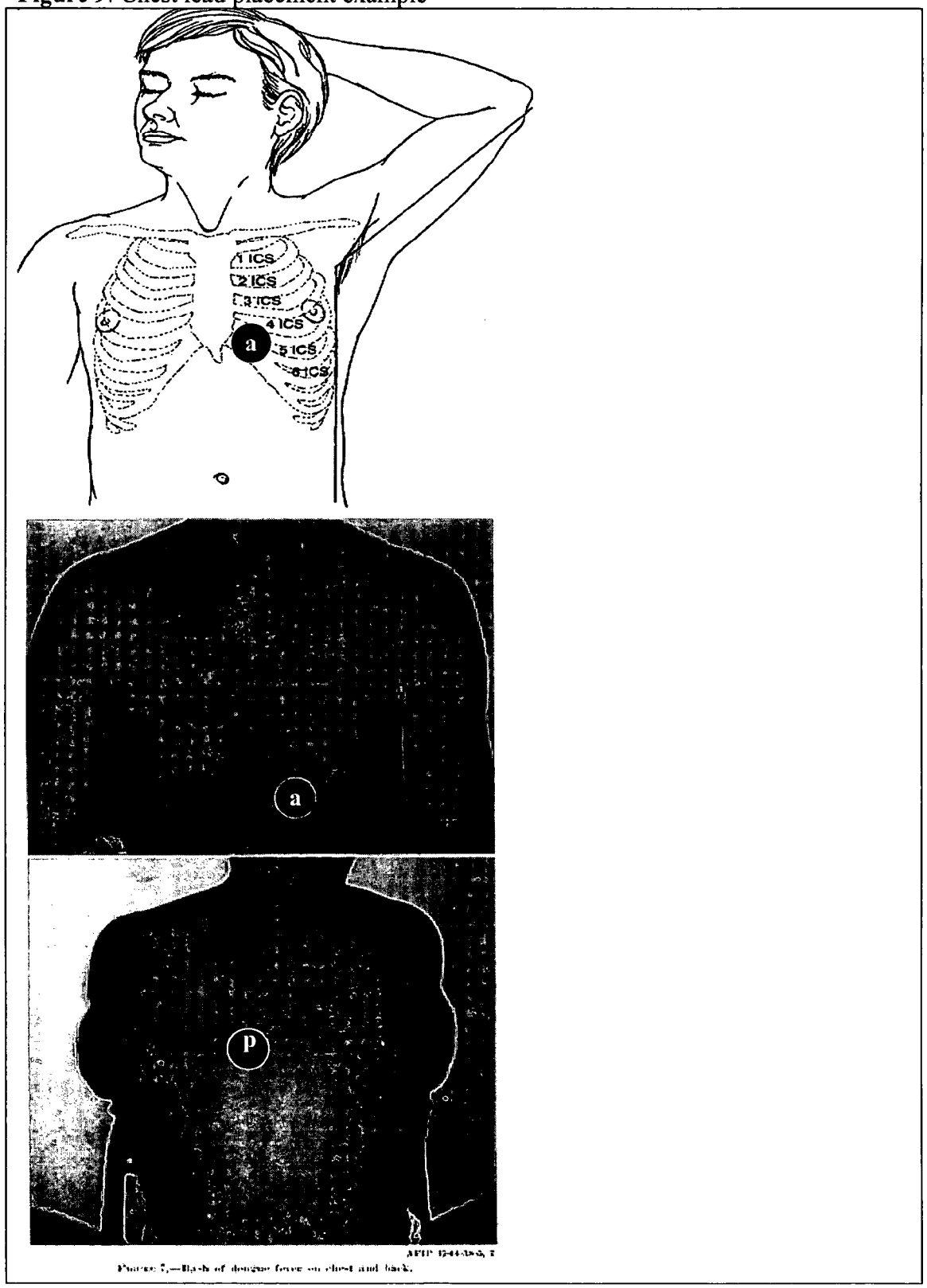

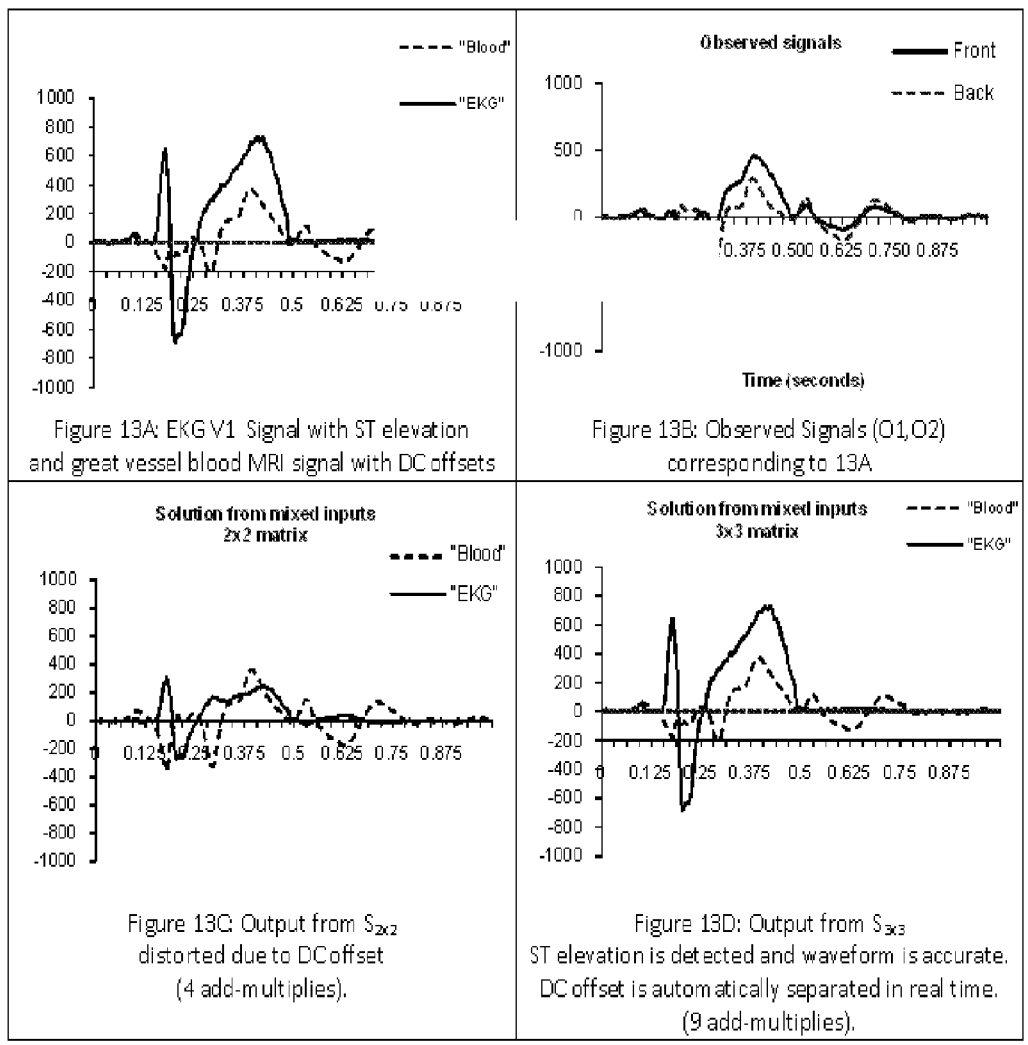

METHOD OF AND SYSTEM FOR SIGNAL SEPARATION DURING MULTIVARIATE PHYSIOLOGICAL MONITORING

CROSS-REFERENCE TO RELATED APPLICATIONS

This application is a continuation-in-part of pending U.S. Utility Application Ser. No. 09/773,167, filed Jan. 31, 2001, which in turn claims priority of U.S. Provisional Application Ser. No. 60/179,192 filed Jan. 31, 2000, both of which are entitled "Multivariate Cardiac Monitor" and are incorporated herein by reference in their entirety.

FIELD OF THE INVENTION

This invention relates generally to medical diagnostic testing and in particular, to a multivariate sensor system and methods of separating superimposed signals from useful physiologic signals such as, for example, magnetohydrodynamic signals from electrocardiographic signals or anterior wall signals from posterior wall signals.

BACKGROUND OF THE INVENTION

Electrocardiographic (ECG) measuring systems generally apply 3 electrodes (to the chest or 10 electrodes (4 limbs and 6 specific points on the chest) to the skin, and, through a differential operational amplifier (OP-AMP), report signal differences between a selected pair of electric contacts or electrodes or between an electrode and a summed reference. The electrical activity thus monitored is generated by a sequence of ion movements in the heart that depolarize (release) and then repolarize (rebuild) an ionic charge distribution across cell membranes, that relates to actuation of contraction of the heart muscle. By convention accepted in the art (with reference to the Figures), a "12 lead" ECG consists of lead pairings I, II, III, avR, avL, avF, v1, v2, v3, v4, v5, and v6, where lead I reports the voltage difference between an electrode on the left arm and another on the right arm; lead II left arm vs. foot; lead III right arm vs. foot; Lead aVR reports right arm vs. combined reference of left arm and foot; aVL left arm vs. right arm and foot; aVF foot vs. left arm and right arm; and the v-leads (v1-v6, v for voltage) represent a series of prescribed positions across the front of the chest vs. the combined reference of left arm, right arm and feet. The American Heart Association and the Cardiac Society of Great Britain defined the standard positions and the wiring for the chest leads v1-v6 in 1938 (Barnes A R, Pardee H E B, White P D. et al. *Standardization of precordial leads. Am Heart J* 1938; 15:235-239). Emanuel Goldberger added the augmented limb leads aVR, aVL and aVF to Einthoven's three limb leads and the six chest leads in 1942, constituting the 12-lead electrocardiogram that is used today. ECG systems are widely used for diagnosis of rhythm changes, metabolic effects, and heart damage.

The ECG signal is commonly described in terms of a sequence of waves called P wave, QRS complex, and the T-wave (originally described by Willem Einthoven, Einthoven W. *Ueber die Form des menschlichen Electrocardiograms. Arch f d Ges Physiol* 1895;60:101-123; Nobel prize awarded 1924). The QRS complex may consist of just R wave or RS or qR or qS, where q, if present, is an initial down-going voltage deflection, R, if present, is the first up-going deflection after the p-wave, and S, if present, is a subsequent down-going deflection (if there are further up-going and down-going waves in the QRS, those are labeled R', S', then R", S", respectively). The P-wave corresponds to electric activation of the small chambers of the heart. The R-wave or QRS complex corresponds to electrical activation of the large chambers of the heart. The T wave corresponds to the staggered end of electric charge redistribution recovery from the electrical activation of the large chambers.

Alternatively, the heart has been modeled for simplicity as a 3D electric dipole represented by orthogonal ECG tracings, and xy, xz and yz loop plots known as vectorcardiograms (VCG's), but VCG's are not relied on and are unpopular clinically for diagnostics or monitoring (E. Frank: *The Image Surface of a Homogenous Torso, Am. Heart J.* 47:757, 1954). Vectorcardiograms are based on 3 orthogonal voltage loop plots representing an electric dipole that changes length and orientation cyclically. The heart is not that simple, so the model introduces error well described in the literature. The vector model is not as powerful at separating unwanted signals as is the multivariate method of this invention, it does not provide ST segment monitoring, and it requires a more difficult set up to be done properly. The underlying model has an estimated 10% error, because the heart is not simply a 3D electric dipole, different lead positions have distinct local information, and more than 4 leads are needed to reproduce the ECG (G. E. Dower, H. B. Machado, J. A. Osbone: *On Deriving the Electrocardiogram from Vectorcardiographic Leads, Clin. Cardiol.* 3:87, 1980; L. Edenbrandt, O. Pahlm: *Vectorcardiogram Synthesized from a 12-lead ECG: Superiority of the Inverse Dower Matrix, J Electrocardiol* 21:361, 1988).

ECG's are used to detect the "R-wave" (the initial up-going component of the QRS). R-wave detection is used to synchronize imaging systems with the position of the beating heart, e.g., for triggering data collection (a strobe-like method to collect data at specific times to effectively freeze the motion of the heart), or for gating the data (to sort collected data in relation to the timing of activation of the heartbeats). There has historically been an assumption that finding the R-wave is the best approach to synchronization of imaging systems, however, the real issue for imaging is to find a time when the heart is filled to a matching volume and position so that data from multiple such times can be combined to form a coherent and consistent image. The intervals between R waves affect this for several cycles. In particular, contractility (the rate and strength of contraction) and the filling time and volumes from preceding cardiac cycles influence the position and timing of the subsequent heart beats.

Following the R-wave and before the T wave there is an early electric recovery period reflected by a voltage called the "ST segment." In certain lead pairings, the ST segment may be depressed or elevated with respect to the baseline of the ECG signal, and in particular with respect to the extrapolation of the P-R segment. It may become depressed when blood supply to the heart is insufficient for the normal metabolism (ischemia), or elevated when there is new or recent damage to the heart muscle (injury current) or transmural ischemia from spasm of a coronary artery, or vice versa if ischemia or damage is visible from the opposite side of the heart. The electrical signals from the heart are not from a point source, but rather represent a summation of contributions from different tissue segments within the heart. Thus ST segment deviations are produced separately by the anterior wall and posterior wall (as well as lateral wall, inferior wall, etc.) which can cause confusion: an anterior lead ST elevation can represent ST elevation produced by the anterior wall and/or ST depression produced by the posterior wall. Thus there is an application of the present invention for routine ECG assessment outside of MRI (in the absence of contamination signals generated by flow in the great vessels and from magnetic field gradients) by applying signal separation to distinguish anterior wall contribution from posterior wall contribution.

Such ST segment deviation is typically evident only in particular lead pairings, which may or may not include standard leads. For example, infarctions on the posterior or right aspects of the heart may be missed in a 12-lead ECG, and an enlarged or unusually positioned heart may not be adequately assessed with the standard 12-lead system. When such circumstances are suspected, clinical practice calls for additional lead placements, e.g., V7, V8, V9, V4R, and V5R.

Continuous monitoring of the ST segment following a heart attack provides a good predictor of the amount of damage. In particular, the intensity and duration of myocardial ischemia (both reflected by the estimated areas under the ST-trend curve) determine the extent of myocardial damage infarct size and ejection fraction in patients with acute myocardial infarction who receive clot-busting therapy (Karel G. M. Moons PhD, Peter Klootwijk MD PhD, Simon H. Meq MSc, Gerrit-Anne van Es PhD, Taco Baardman MD, Timo Lenderink MD, Marcel van den Brand MD PhD, J. Dik F. Habbema PhD, Diederick E. Grobbee MD PhD, Maarten L. Simoons MD PhD. *Continuous ST-Segment Monitoring Associated With Infarct Size and Left Ventricular Function in the GUSTO-I Trial, Am Heart J* 138(3):525-532, 1999). Also in association with ischemia or injury, the T-wave may change form or invert.

Prior art solutions to problems encountered during electrocardiography include using light emitting diodes to flag poor electrode contact because electrodes may become detached during data collection. One device uses a microprocessor to trigger an alarm when a drop in impedance below a threshold value is detected, simultaneously activating an automatic search for alternative lead combinations that may be intact. Another device applies additional leads to use as alternates depending on patient size, embedding the leads in a uniformly weighted pad. Another prior art device enables amateur application of multiple leads in the general region of the heart for computer selection of a lead that appears to have correct position.

Despite the application of multiple leads, these prior instruments and methods merely provide alternates for selection of a preferred electrode set to use in the conventional manner of reporting signal differences between a pair of voltage sources and/or require particular lead placements. They assume that there is a best subset of standard combinations and standard positions to use for gathering a usual ECG signal. In normal healthy subjects, with standard lead placements, that may be true; but diseased patients generally have changes in the heart resulting in changes in the ECG signal from standard lead pairs. In particular, myocardial infarction, or heart attack, typically results in loss of R-wave height.

Triggering and gating are impaired if the R-wave is not the expected tallest narrow spike in the ECG. Taller R-waves may be found if observed from other, non-standard, electrode locations. To address the problem of failed ECG triggering, filters have been applied ECG signal to reduce signal at frequencies not of interest; that can help but does not reliably resolve the problem. In particular, filtering removes signal based on frequency content, but the frequency content of aortic pulsation is substantively similar to the frequency content of ST-T waves, and therefore the aortic pulsation artifact of concern in MRI cannot be corrected by filtering without distorting the T-wave and interfering with ability to monitor ST-T wave changes.

Arand, et al. (U.S. Pat. No. 5,817,027) disclose a method of identifying temporal components of an EKG (not within an MRI), such as R-waves and T-waves by matching those components to "templates", which requires the components to be in standard form and appearance. The method uses signal averaging, which blurs random fluctuations and helps suppress uncorrelated noise, but which actually reinforces systematic signals such as the aorta signal seen in MRI which is highly synchronous with the EKG (the MRI aortic signal artifact is not random noise or a mere motion artifact.) That technique does not apply any source separation nor extract information from different sensitivities of sensors to sources of different physical locations of origin. To the extent that the appearance of aorta pulsation signal would be modified by her method, the ST-T wave would also be modified; for the bulk of shared frequency content in ST-T wave and aorta pulsation signal her method has no ability to separate the two.

Even with a normal ECG, there are "electrically silent areas" of the heart in which ischemia or injury may occur without the usual evidence of ischemia or injury in the standard lead position ECG, as mentioned above. Patients with enlarged or repositioned hearts may be better evaluated from non-standard lead positions. As a subject breathes in and out there is a "baseline artifact" which may interfere with standard interpretation of the signals, but which may prove useful in reporting the phase of breathing. Also, there is a variation in the interval from one heart beat to the next ("R-R interval"), allowing increased or decreased filling of the chambers, and thus changes in the size of the heart that may impair the goal of ECG triggering or ECG gating. In response to changes in filling, the heart changes its contractility (strength and rate of contraction) for the subsequent cycle(s). Also, incorrect placement of the chest leads v1-v6 can produce false indications of ischemia or infarction.

Magnetic Resonance Imaging (MRI) is an example of an imaging device that uses the height of the R-wave as a trigger to synchronize data collection to the heartbeat activation and effectively freeze the motion of the heart. Early MRI studies took over 20 minutes to build one or more images of the heart as a composite from multiple heartbeats. New MRI systems can acquire images in less than 20 seconds, with some methods completing an image in less than half a second. With such capabilities, it is now possible to follow changes in the heart from beat to beat. For example, one may observe the arrival of a blood-born contrast agent and determine if there are areas of impaired blood delivery. Such methods need, more than ever, a reliable detection of the electrical activation of the large chambers of the heart. Newer MRI systems also have higher magnetic fields than in the past, resulting in greater induction of an electrical signal due to the pulses of blood moving along in the great vessels. That signal generally adds to the normally lower "T-wave." Consequently, the R-wave is often not the tallest wave. Also, MRI applies controlled magnetic fields to encode the data it collects for imaging. The newer faster imaging methods use improved hardware to change the magnetic field more quickly, inducing higher, narrower, electric signals that commonly obscure the R-wave. Baseline artifact related to the respiratory cycle may be exaggerated.

It remains desirable to perform accurately medical diagnostic testing on the heart, in the presence of disturbing signals, or with imperfect lead placements, such as in settings where time or expertise are limited. Likewise it remains desirable to obtain diagnostic signals when signal character is non-standard due to disease, or when the signal changes after the subject is advanced into an imaging system. Also, it is desirable to extract information about the respiratory cycle.

SUMMARY OF THE INVENTION

The present invention provides a method of and system for separating physiologic signals produced by a live body organ from superimposed contaminating signals simultaneously acquired during physiologic monitoring.

It is an object of this invention to provide a means for rapid placement of electrical contacts.

It is also an object of this invention to provide a means for collecting and analyzing data from multiple contacts in order to characterize the electrical activation from specific sources. No orthogonality is required in electrical lead placement.

It is an object of this invention to generate one or more signals useful for diagnostics, triggering, or gating.

It is a further object of this invention to assess respiration.

It is still a further object of this invention to provide a simple and rapid means of forming multiple electrical contacts for diagnostic monitoring.

It is another object of the present invention to reliably represent the electrical activation of the large chambers of the heart, especially the narrow, tallest peak used for triggering imaging systems.

It is another object of the present invention to provide a method and apparatus to identify ischemia or injury to the heart.

It is an object of the present invention to report the results in a synthetic signal.

It is yet another object of the present invention to provide a method and apparatus to compare signals inside and outside the imaging system.

It is another object of the present invention to provide a method and apparatus to identify the electrical activation of the small chambers of the heart.

It is still yet another object of the present invention to provide a method and apparatus to identify and flag aberrant heartbeats.

It is yet a further object of the present invention to provide a method and apparatus to analyze cycle lengths to enable triggering based on comparable filling periods, particularly for cases of rhythm disturbances, such as atrial fibrillation, which currently have been considered relative contraindications to gated imaging.

It is another object of the present invention to provide a method and apparatus to analyze the "respiratory artifact," and to identify the phase of breathing, and to provide a corresponding signal for control.

The problems of performing diagnostic testing on the heart are solved by the present invention of a new electrode-based monitoring system that uses multiple electrodes to create a multivariate characterization of the status of the heart (or other organ). An example of multivariate characterization is the description of a person in terms of height, weight, sex, eye color, interests, culture, education, and so on. The present invention collects multivariate data from contacts distributed on the body, and derives from the multivariate data a synthetic or composite signal for specific purposes. The present invention takes advantage in particular of the proximity effect, whereby the sensitivities of a sensor to different signal sources are different for different sensors, due in part to the fact that signal contributions are stronger for sensors closer to a particular source. A synthetic or composite signal refers to a signal that is computed or derived from measured data, but may be different in form. A synthetic ECG is a signal that represents and looks like a standard ECG but is computed or derived from data that may be non-standard.

The present invention analyzes data from multiple leads to generate a multivariate characterization of the events of interest. In the preferred embodiment, wire from an electrode is paired and twisted with wire from the same location but not making electrical contact with the chest. The wire is resistive to reduce induction of stray signals, e.g., a 24 inch carbonized wire with 200,000 ohms resistance (impedance) end to end. The wires not making contact with the chest may be bridged by resistive wires to make comparable current loops that do not include the current sources produced inside the body, but do capture signals generated outside the body due magnetic flux through current loops such as occur during gradient switching or motion.

A plurality of such lead pairs is applied to the anterior and/or posterior and/or side(s) of the chest wall as an array, harness, vest, partial vest or shoulder holster. These leads go to a battery-powered magnetic field-compatible processing unit. Lead pairs go to a differential operational amplifier, preferably an instrumentation amplifier, to eliminate stray signal common to both (instrumentation amplifiers provide 100 dB common mode rejection). Alternatively, leads may be used that are not physically paired to a matched location; instead, pairings with one or more common references may be used for common mode rejection. Optionally additional levels of common mode rejection may be applied to the resultant signals from electronically paired leads.

All processing may be completed in a first processing unit, which may be battery-powered, or the signals may be multiplexed and converted to optical or other forms of signal for transmission to a second processing unit. The linkage between such processing units is characterized by a transmit end and a receive end. The conversion of signal for transmission may utilize an analog to digital converter (ADC), which may be a stand alone component or integrated with a microprocessor. The optical cable linkage may be plastic, e.g., passing 890 nanometer short wavelength light to support up to 125 megabits/second data transmission. The receive end may use an integrated circuit transmitter assembly to convert the data stream to a form useful for analysis, optionally with sigma-delta modulation, for a target bandwidth of 0.01-200 Hertz (low frequency near 0.3 Hertz reports respiratory effects; high frequencies contribute to signal fidelity but also noise; optionally the circuit will include pre-charging to increase the low frequency response time at start-up).

During a brief, repeatable (if necessary) training phase, the processing unit compares observed multivariate signals to a model and/or training data (also referred to herein as "template" signals or data) to identify desired features of the signal and to determine coefficient values of a separability operator S, which then may be applied in real-time to subsequent observed signals to separate the signal sources on distinct channels. Training data/template signals may be any combination of historic, empiric, model, or actual data from others or from the subject to be observed. Desired features may include electrical activation of the smallest chambers (P-wave timing), electrical activation of the large chambers (R-wave timing, QRS form), baseline deviation of early repolarization (ST-segment shifts), staggered repolarization (T-wave form), respiratory cycle from baseline artifact, temporal averages and beat-to-beat variations, and also waveforms contributing to the contaminating signals, e.g., arterial pulse waveform from oximetry reflecting the pattern of MRI signal from blood flow in the great vessels.

The multivariate data may be processed first to reduce or eliminate bad data lines, artifacts, and noise. For example, individual data lines not corresponding to expected signal patterns may be eliminated or modified. The multivariate data may be constrained to eliminate multivariate combinations or regions not generated by physiologic signal. The constraints may be based on a model, experimental, a priori data, a standard 12-lead ECG from that patient, a standard set of constraints from experience, or data obtained inside and/or outside the interfering environment (e.g., with and without the static magnetic field, and/or the gradient switching). The residual multivariate data may be fit to a parametric model that includes a representation of the important features, the multivariate data may be analyzed statistically for correlation with specific features, or a neural network may be applied to extract the desired features. A synthetic signal is then generated showing the desired features more clearly, optionally corresponding to specific standard lead combinations, and conforming to simple rules such as: R-wave is highest peak. Alternatively, the R-wave may represent the expected height for a specific ECG lead combination, but with a superimposed spike, analogous to a pacemaker spike, so that the highest net peak coincides temporally with electrical activation of the large chambers. In addition, small spikes may be added to the out-going signal following the standard presentation, to represent the numeric value of ST segment deviation, e.g., two and a half up-going spikes after the T wave to indicate 2.5 mm ST elevation.

BRIEF DESCRIPTION OF THE DRAWINGS

The present invention together with the above and other advantages may best be understood from the following detailed description of the embodiments of the invention illustrated in the drawings, wherein:

FIG. 9 is an illustration and photograph indicating the placement of an anterior and a posterior sensor in one exemplary embodiment of the invention;

FIGS. 13A-13D are graphs demonstrating an ability of an expanded separability operator S matrix to correct errors attributable to DC offsets.

DETAILED DESCRIPTION OF PREFERRED EMBODIMENTS

Figure 1:
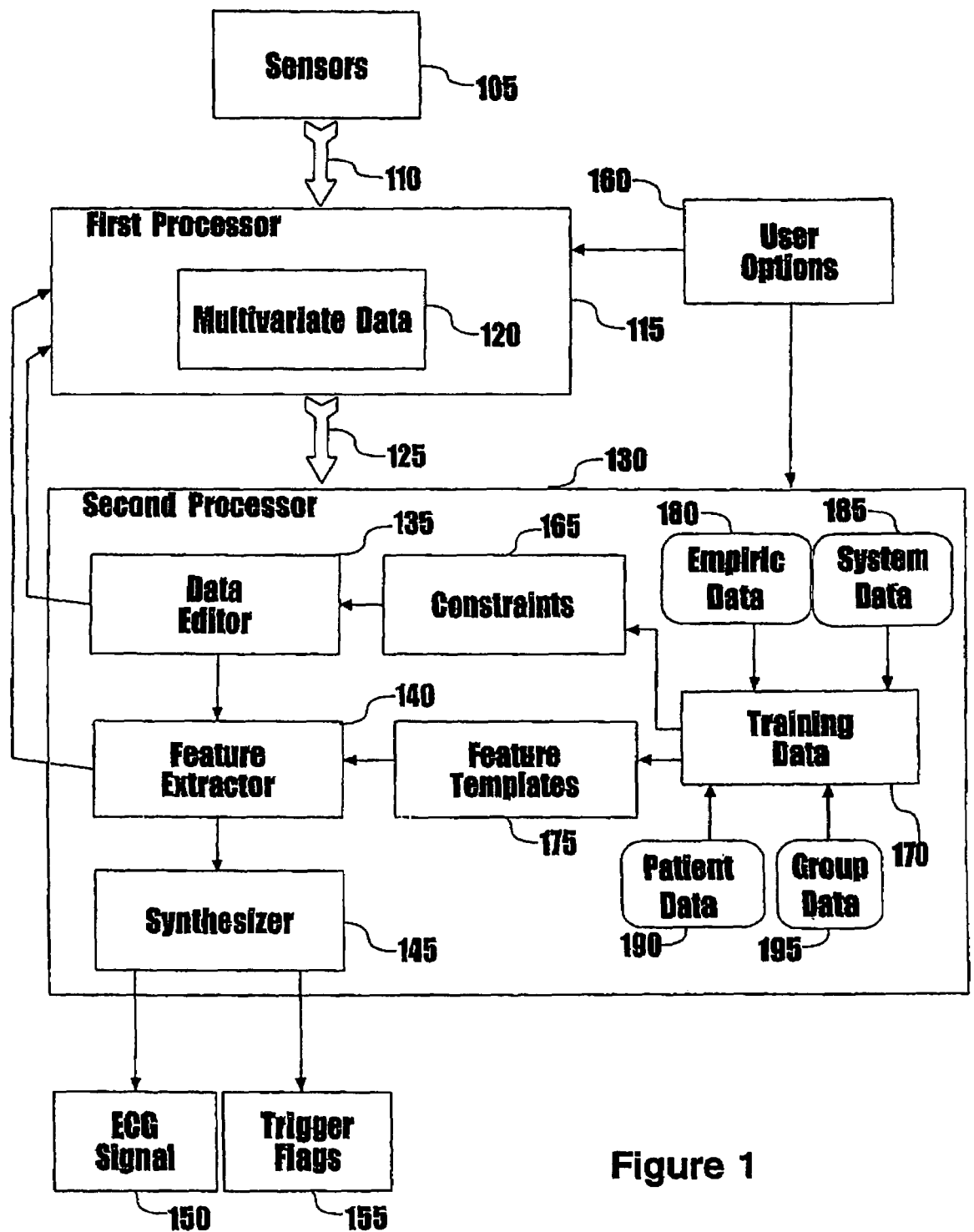
FIG. 1 is a block diagram of the multivariate characterization monitoring system according to principles of the invention.

A preferred embodiment of the present invention incorporates therein a monitoring system that uses multiple electrodes to create a multivariate characterization of the status of the heart. During a training phase, the system utilizes template signals (the expression "training data" is used interchangeably) to compute values for a separability operator S that may be applied in real-time to subsequent observed data to separate distinct, superimposed signal sources from a desired physiologic signal.

The template signals are used in the training phase to calibrate the system to separate mixed signals from a specific subject. Subjects differ in various ways, including height, distribution of muscle mass, flow in great vessels, and orientation of the electrical activation of the heart in relation to the other signal sources. The use of template signals takes less than one second, and can be repeated if desired to monitor for drift if conditions change radically (e.g., marked drop in blood flow). The use of templates involves more than a simple computer recognition of a signal that is clear to an observer, but rather it provides a calibration that serves to identify the impact of individuality in sensor placement and body form (both of which are generally stable during an imaging session, but differ from case to case). The method is adaptive to these differences yet robust to detection of physiologic changes that are desired to be observed, such as ST segment elevations, and changes in the signals we need to separate, e.g., cardiac signals vs. flow vs. signal from magnetic field gradients.

While the description that follows is concerned with a preferred utilization in ECG monitoring, the method of the present invention is not intended to be limited to cardiac monitoring.

The separability operator S is described below is preferably a matrix of separation coefficients that collectively specify a model of the conditions of physiologic and external signal sources encountered during physiologic data acquisition. Applying the separability operator S to subsequently observed multivariate signals (i.e., discretized data representations thereof) separates the distinct signal sources on multiple channels, permitting graphical representations of a desired synthetic or composite signal, such as an ECG, for a wide variety of specific purposes. A synthetic ECG (as used herein) is one regenerated or constructed by computer, in this case based on specific information extracted from the multivariate data. The synthetic ECG data is used to identify specific features such as timing of the electrical activation of the large chambers, to specify an R-wave in the computed or simulated signal output, and/or to monitor depression or elevation of ST segments.

As the term is used herein, "template" signals are waveform characterizations and/or rules used to train the monitoring system. Template signals serve as measures of success in computing a separability operator S, not simply for waveform recognition as employed in prior art heartbeat classification systems. The separability operator S provides a mathematical means for real-time separation of superimposed contaminating signals acquired during physiologic sensor monitoring from a desired signal, such as flow signal in the aorta from an ECG signal or component thereof, or even anterior wall ECG signal versus posterior wall ECG signal. During cardiac magnetic resonance imaging, for example, a plurality of signals are superimposed in the signals observed by the EKG leads, such as, for example: (1) the (desired) EKG signal; (2) signals from blood flow (magnetohemodynamic signal) in the great vessels; and (3) signals from gradient switching.

Each of the signals observed at the physiologic sensors are affected by the sensitivities of the sensors to the distinct signal sources, e.g., due to the proximity of each sensor to the signal sources. As will be described below, the separability operator S utilizes the different sensitivities of the sensors to the different sources to enable source separation.

During the training phase, observed multivariate signals are compared to training data to identify desired features of the signal, e.g. electrical activation of the smallest chambers (P-wave), electrical activation of the large chambers (R-wave), early repolarization (ST-segment), peak repolarization (T-wave), respiratory phase from baseline artifact, and wave morphologies. Likewise the processing to compare with training data and/or measured reference data can be used to identify undesirable features such as aortic pulsation and gradient switching artifacts. Training data comprise multivariate signals acquired for this invention, empiric data, standard signals acquired from standard positions, on the same patient as a preliminary evaluation, on the same patient by scanning in a prior standard ECG, and/or on different or made up subjects. Training data may also include concurrent or historic data collected on gradient effects and magnet effects. The training data represent the features of interest, expected ranges of values and covariance as a function of time, and expected signal disturbances.

Whereas an objective of the output of this invention is source-separated signal and elimination of the contribution of contaminating signal sources, for ease of use on legacy systems, the present invention can apply additional rules in the generation of the synthetic signal produced from the identified features to show the desired features more clearly optionally to promote clarity such as: R-wave is highest peak, baseline is flat, P-wave is distinct, ST-segment deviation if present is clear and measurable in millivolts (or millimeters corresponding to voltage) deviation from the flat baseline. Optionally, a sequence of voltage spikes following the T wave will count how many millimeters or tenths of millivolts of ST segment deviation (using half-height for half a millimeter). Thus the synthetic signal is a signal generated by computer containing key features of interest such as P-wave, QRS, ST-segment deviation, T-wave, in a clean form. It may represent any selected view such as any of the standard 12 lead combinations or extended alternate views that may show maximal R wave or maximal ST segment deviation. The synthetic signal allows presentation of "in-between" or interpolated views that correspond better to conventional standards than the possibly non-standard positions observed.

The heart generates current distributions, from its movement of ions, resulting in voltages on the chest that are basically a continuous function of position sampled. After source separation, signals are identified that represent select "views" of the heart. The potential number of views is infinite, but forms a continuum. It has been determined that the signal that would have been observed at an un-sampled intermediary position may be estimated accurately from the signals at neighboring positions; the correspondence between multivariate observations and standard lead position data enable prediction of the standard views from the multivariate observations, e.g., by curve fitting.

The computed results may be expressed as a synthetic analog ECG signal. Also, the predicted signal need not be constructed directly as voltages vs. time. Alternatively, it may be constructed from basis elements reflective of the desired information content: timing of the P wave deflection, interval between P and QRS, timing of the R wave deflection, severity of ST segment displacement, presence or absence of T wave inversion. Such information elements suffice to generate a simulation signal that accurately reflects those variables based on the multivariate data, but presents them as a clean, very easily understood standardized view, free of noise and artifacts.

The user may elect to preserve R wave height and/or form in the simulated ECG. Then, rather than making the R-wave the maximal peak by design, a narrow upward spike may be superimposed, similar to the signal of a pacemaker, so that legacy R-wave detectors will unfailingly follow the timing of the electrical activation of the large chambers of the heart. In addition to visually communicating specific information, the simulated ECG provides a standard input to pass the accurate interval tracking to legacy systems such as threshold R-wave trackers on MRI systems.

The major components of the present invention are shown in FIG. 1. First, a plurality of sensors 105 detect observed physiologic signals. The positioning of the sensors 105 are not constrained to conventional orthogonal placement. Those observed signals are linked by linkage 110 to a first processor 115. The first processor 115 converts the signals to multivariate data 120. The multivariate data 120 from the first processor 115 may be linked by linkage 125 to a second processor 130. The second processor 130 applies a data editor 135, a feature extractor 140, and an output synthesizer 145 to the multivariate data 120, to create signal output 150, and/or trigger flags 155 for triggering or gating and/or accounting for rhythm changes. The first processor 115 may receive control input from user options 160, from the data editor 135, and from the feature extractor 140. The data editor 135 may receive control input from constraints 165, which may receive input from training data 170. The feature extractor 140 may receive input from the feature templates 175, which may receive data from the training data 170. The training data 170 may receive data from user options 160, empiric data (180; data that serves as a model of co-variant ranges, patterns, and parameters), system data (185; data from equipment such as MRI indicating what signals or noise the equipment may generate or induce), patient data (190; data from the patient indicating target signal co-variant ranges, patterns, and parameters), and group data 195; data from a group or population indicating expected co-variant ranges, patterns, and parameters). The output synthesizer 145 may receive control input from user options 160.

Details of the sensor system are shown in FIGS. 2A-2D. In a preferred embodiment, wire from an electrode that makes contact with the chest wall is paired and twisted with wire electrically isolated from the skin. The wires from these paired locations are resistive to reduce pick-up of stray signals, e.g., 60 cm carbonized wires with 200,000 ohms impedance end to end. A plurality of such lead pairs may be applied to the anterior and/or posterior and/or side(s) of the chest wall as an array, harness, vest, partial vest or shoulder holster. The number of contact points is at least two, and may be distributed to include chest wall anterior and/or posterior and/or lateral to the heart. Alternatively, single lead wires may be used. The purpose of the paired wire system, explained further below, is to eliminate signals that are produced by gradient switching and motion (magnetic flux through wire loops).

Figures 2A, 2B, 2C:
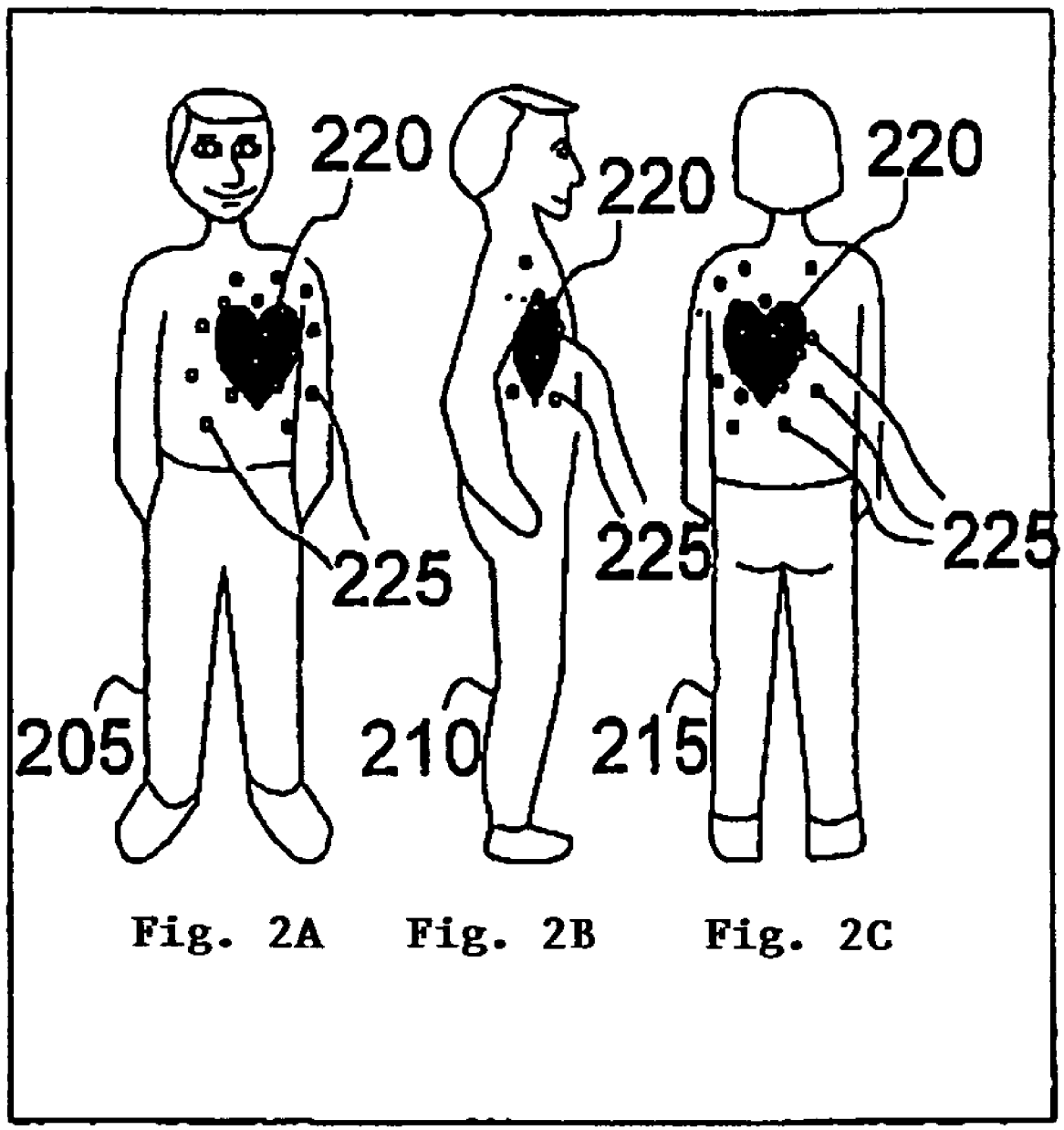
FIG. 2 shows details of the sensor system.

The wire leads go to a battery-powered magnetic field-compatible processing unit (both the wire leads that contact the skin, and the wire leads that optionally are paired with contacting leads but do not make skin contact). The leads that do not make skin contact provide signals not related to the ECG, so that such signals, when found also on the skin-connected leads, can be eliminated. This operation is called common mode rejection, or CMR. All processing may be completed in that unit, or the signals may be multiplexed and converted to optical or other signal for transmission to a second processing unit. With reference to FIGS. 2A-2C, a patient anterior view 205, posterior view 210, lateral view 215 each illustrate a plurality of sensors applied in contact with the skin surface. The present invention provides great latitude as to the number, distribution and arrangement of the sensors on the skin, with no requirement for orthogonality, regular spacing, or alignment in rows or columns. The preferred distribution of contact points includes anterior 205, posterior 210 and lateral 215 contacts on the thorax, above, at, and below the general level of the heart 220.

Figure 2D:
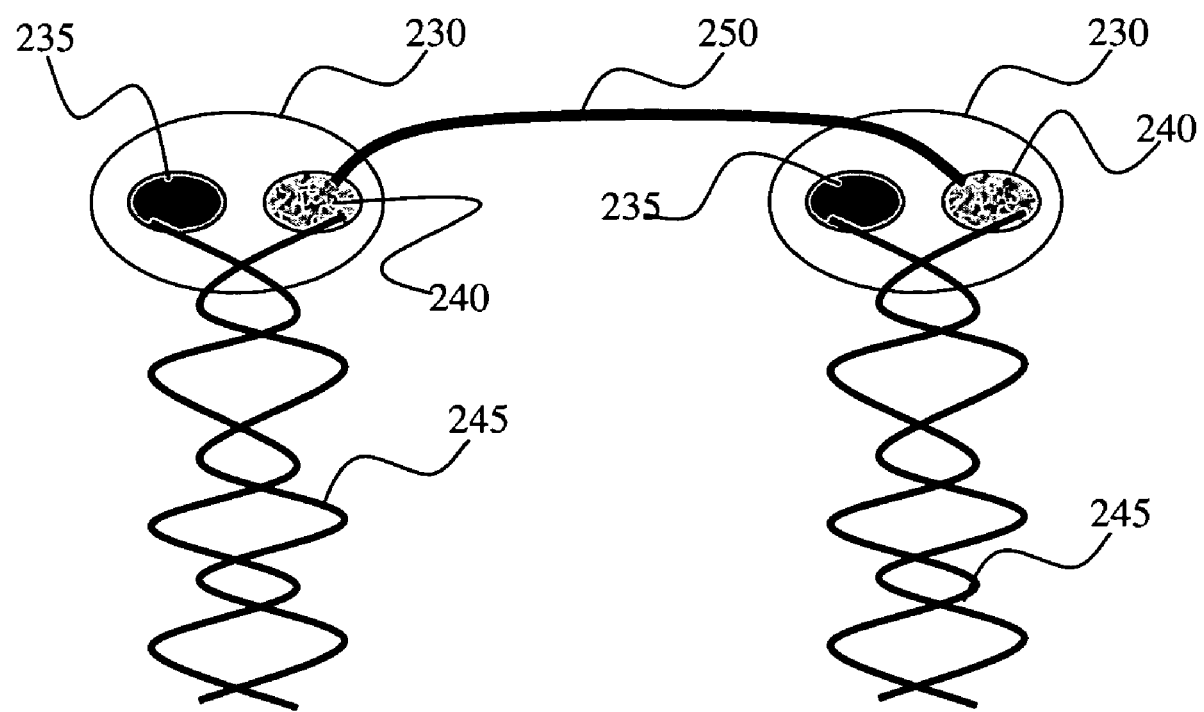

With reference to FIG. 2D, in a preferred embodiment each sensor 220 has a plurality of terminal contact points 235, 240 for wires 245. The terminal contact points are of two types: a through-type contact 235 that passes through the electrode patch of the sensor 220 to make electrical contact with the patient's skin, and optionally a null-type contact 240 that is electrically isolated from the skin. Resistive bridging electric connections 250 may connect the null-type electrodes 240 to establish circuits that enclose similar geometric areas as those that pass through the EKG wire loops and the patient, and thus they can detect the magnetic flux signal for signal separation of those voltages that are from magnetic field changes that occurs due to magnetic flux through the wire loops. The sensor positions may be maintained, for example, by adhesive, one or more elastic straps, or an external vestment.

Figure 3:
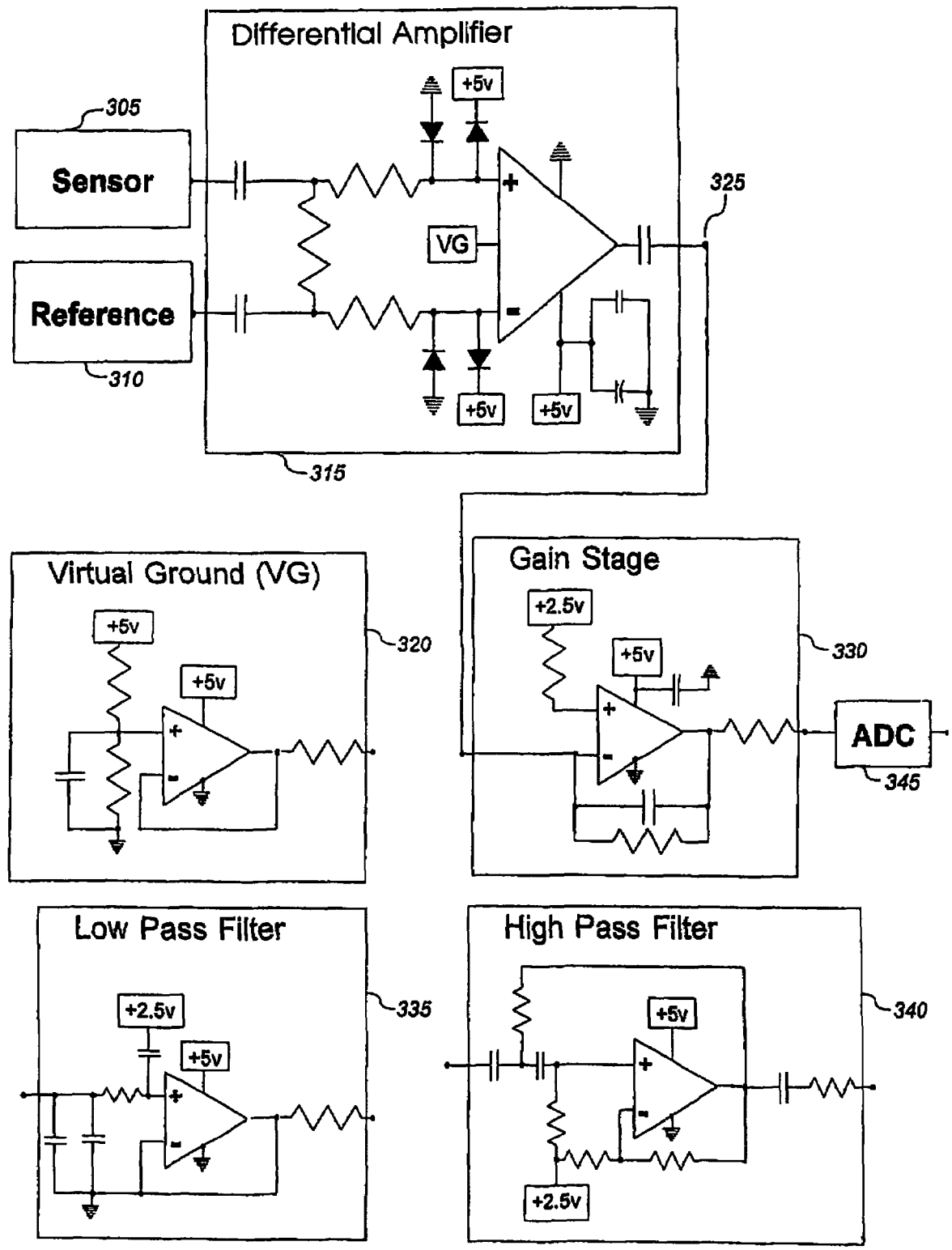
FIG. 3 shows details of the first processing unit.

Details of the first processing unit are shown in FIG. 3. Linkages from a sensor 305 and a reference 310 connect to a differential amplifier 315, or an instrumentation amplifier, for common mode rejection of unwanted or stray signals present in both linkages. The reference 310 can be a said null terminator, or a single common sensor serving as reference, or a member of a set of sensors. For example, all possible pairings of sensors may be used. The center terminal of the differential amplifier may be linked to the output from a virtual ground generator VG 320, to enable DC bias to place the incoming voltages in an appropriate range for the differential amplifier 315. The output 325 from the differential amplifier may go to a gain stage 330 to prepare the signal for analog to digital conversion. Optionally, a low pass filter 335, and/or a high pass filter 340 may be placed before and/or after the gain amplifier 330, to constrain the signal to frequencies of interest. Optionally, the DC offset from the virtual ground generator VG 320, and/or the amount of amplification in the gain stage 330, and/or the pass levels for the filters 335, 340, may be set by remote linkage from a second or third processor or from user input. The signal next undergoes analog to digital conversion.

The analog-to-digital conversion may be accomplished by an analog to digital converter or ADC 345, which may be a stand alone component or integrated with a microprocessor, e.g., Microchip PIC16C73B, or preferably with sigma-delta encoding and 15 bit resolution. The ADC converts the set of signals from the sensors to digitized multivariate data.

Figure 4:
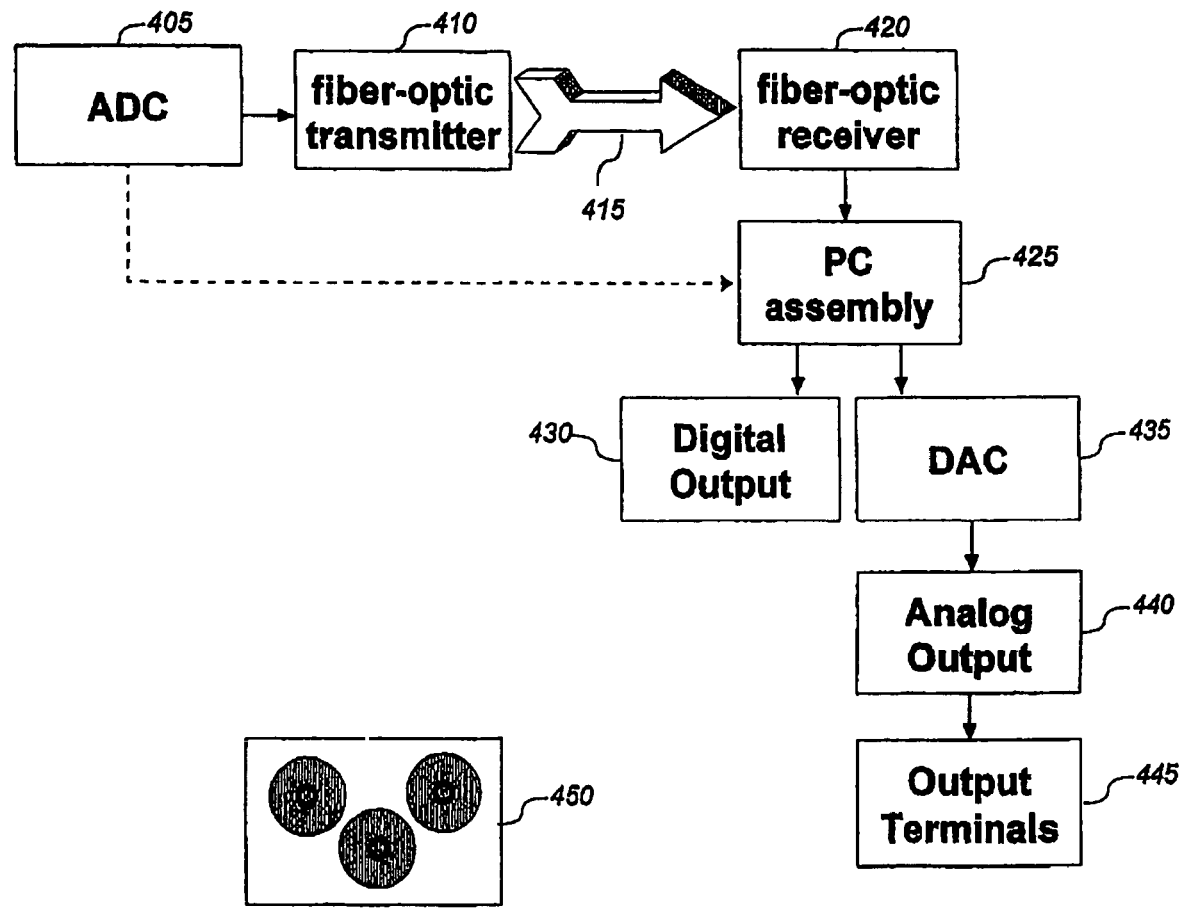
FIG. 4 is a block diagram of the management of the multivariate data.

Management of the digitized multivariate data from the ADC is shown in FIG. 4. Although not required for the main objectives of the present invention, the preferred embodiment links the digitized multivariate data from the ADC 405 are linked to a fiber-optic transmitter 410, transmitting the multivariate data over a fiber-optic linkage 415 to a fiber-optic receiver 420. The fiber-optic transmitter can use a light emitting diode or a dedicated encoder, e.g., applying 890 nanometer short wavelength light to support up to 125 megabits/second data transmission. The fiber-optic linkage 415 avoids further pick-up of stray signal, and allows further processing to be placed remote from interfering equipment such as an imaging system or strong magnetic fields.

The fiber-optic receiver 420, or the ADC 405 directly, is linked to a PC assembly 425 for analysis of the multivariate data features and synthesis of output. The output from the PC assembly 425 may be used in digital form, with digital outputs 430 for ECG and/or respiratory triggering or gating or other condition flags. In particular, one condition flag may indicate end-expiration, and thus return of the diaphragm, and the heart riding on the diaphragm, to a standard position. Another condition flag may report whether the preceding R-R interval was within tolerance of the mean R-R interval for that patient. That serves to indicate that the filling time from the preceding interval is standard, and so the heart volume at the current trigger is standard for that patient (thus providing a mechanism for reliable triggering or gating even in the presence of marked rhythm disturbances such as atrial fibrillation). Also, the output from the PC assembly may be linked to a digital-to-analog converter 435, producing analog output signal 440. The analog output signal 440 may be linked to output terminals 445 similar to those on standard electrodes, so that an imaging system requiring ECG signal may interface to these output terminals 445 as if they were standard electrode snap connectors. The terminal electrodes are shown from top view 450, and one in side view 455.

Figure 5:
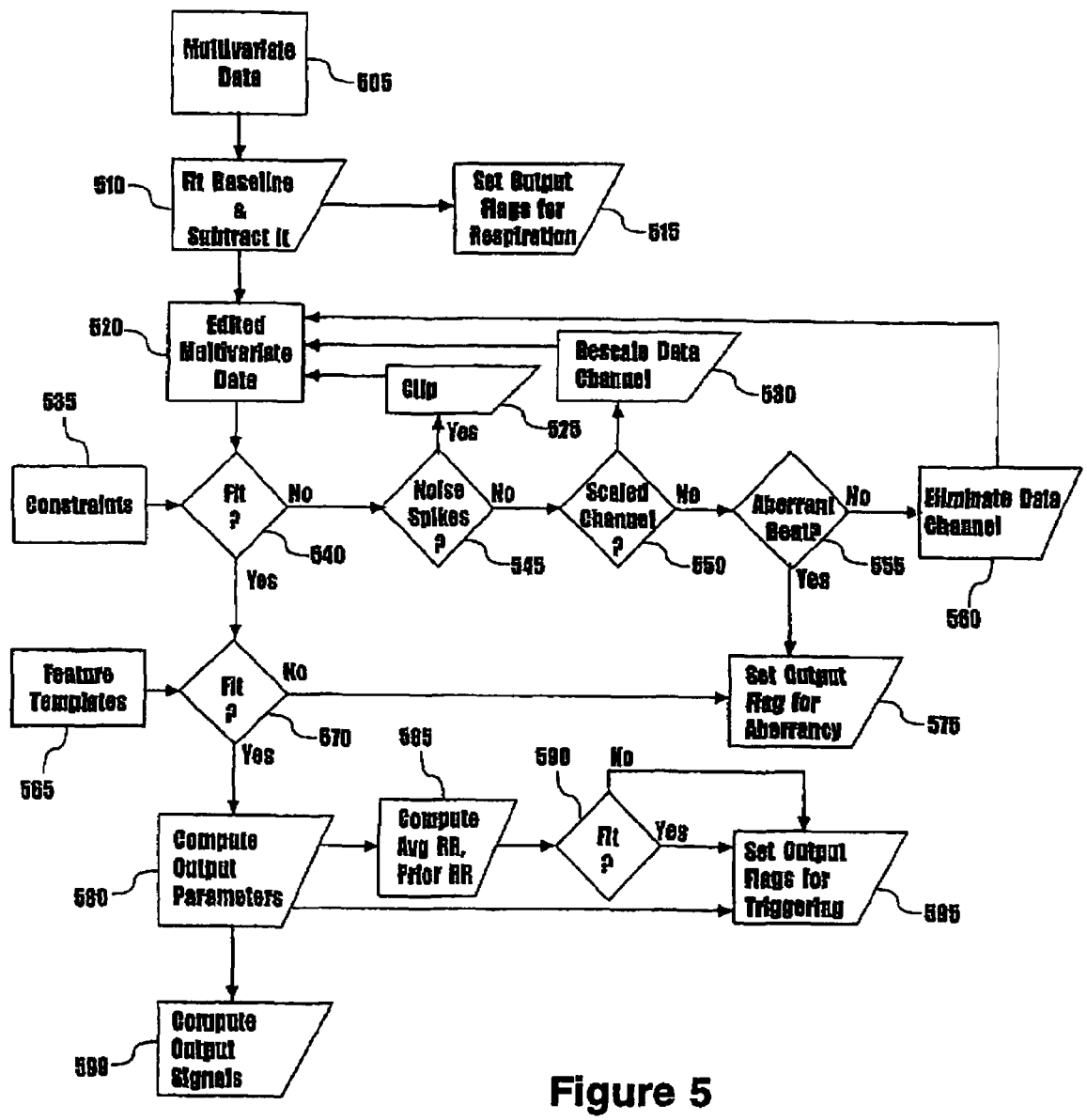
FIG. 5 is a diagram of the data processing logic.

Whereas a preferred embodiment relies on real-time application of a separability operator, the invention also allows optionally for logical processing to enable other enhancements. Logic operations and data flow for an embodiment of the data processing are shown in FIG. 5. Multivariate data 505 is analyzed by low frequency curve fit with median filter to fit the respiratory baseline artifact and subtract it 510. The results of the baseline fit are used to set output flags for respiration status 515. The flags are cleared when read, and reset by further data according to the present status. The baseline subtraction results in edited multivariate data 520. The edited multivariate data 520 also results from clipping spikes (525; if data deviate from expectation momentarily, e.g., apply median filter, rescaling (530; if data agree in form but differ in amplitude, and data channel elimination (560; if the data from a sensor is unreliable.) Based on the edited multivariate data 520 and constraints (535; which reflect expected temporal evolution of the multivariate data), a comparison 540) determines if the edited multivariate data 520 fit the constraints 535. If they do not fit 540, the data is examined further for noise spikes 545, scale change 550, aberrant beat or ectopy 555, or unreliable data channels 560. If the edited multivariate data 520 does fit 540 the constraints 535, then feature templates 565 are fit 570 to the data. If the shape and/or timing parameters do not fit well, the data may yet be flagged as aberrant 575. If the fit 570 is good, then output parameters 580 are computed. These parameters describe the timing and/or shape of important signal components (QRS, RR-interval, ST-segment deviation, etc.) From the output parameters 580, average RR interval, standard deviation, and last RR interval 585 are computed. The last RR interval is compared to the statistical summary 590 to determine if the filling time offers a standard anatomic filling for imaging, and triggering flags 595 are set accordingly. The timing and/or predicted timing of the R wave activation also sets triggering flags 595. In addition to setting flags, the computed output parameters 580 are applied to synthesize output signal 599. The output signal 599 reports a clean ECG signal in any desired view with a spike superimposed to mark the R wave trigger, with ST segment deviations corrected for baseline artifact, machine effects (via constraints, which are built from information about the patient, expected signals, gradient effects, and magnet effects, and noise. Optionally, the ST-segment deviations and/or other features may represent a running average over a user-selected time period. Also, a series of spikes may be added after the T wave to count out the amount of ST segment deviation as described.

Figure 6A:
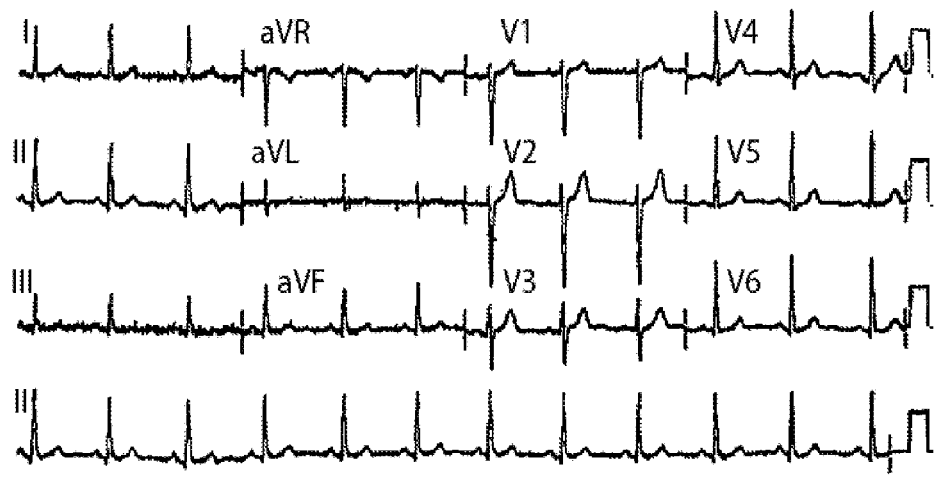
FIGS. 6A-6J show examples of signals from standard ECG's.

A normal 12 lead ECG is shown in FIGS. 6A. The data is organized to show several beats from each lead, as labeled, plus a longer "rhythm strip" from lead II as the bottom row. Note the noise in leads I, III, aVL, all relating to low quality signal from the left arm contact. Multivariate evaluation would provide alternatives, so the noisy data line could be circumvented. Each P wave is followed by a QRS. The shape of the P wave is normal for the subject; in lead II the height is less than 2.5 mm, and the width is less that 0.11 seconds. The rate is between 60 and 100/minute with less than 10% variation. The P-R interval (beginning of P to beginning of R is steady and between 0.12 and 0.20 seconds. The QRS heights are positive in leads I and avF, indicating a normal "axis" or principle frontal direction of activation, and nowhere are they high enough to indicate heart enlargement. The width of the QRS is less than 0.12 seconds. The shape is normal for the subject; no significant Q waves, no extra components. The QT interval (beginning of QRS to end of T wave), adjusted for the rate by dividing QT by the square-root of the preceding RR, is 0.42 seconds. The ST segment is not elevated or depressed over the baseline extrapolated from the PR segment. The shape of the T wave is normal for the subject; not too tall, not generally flat or inverted, and generally in the same direction as the QRS.

Figure 6B:
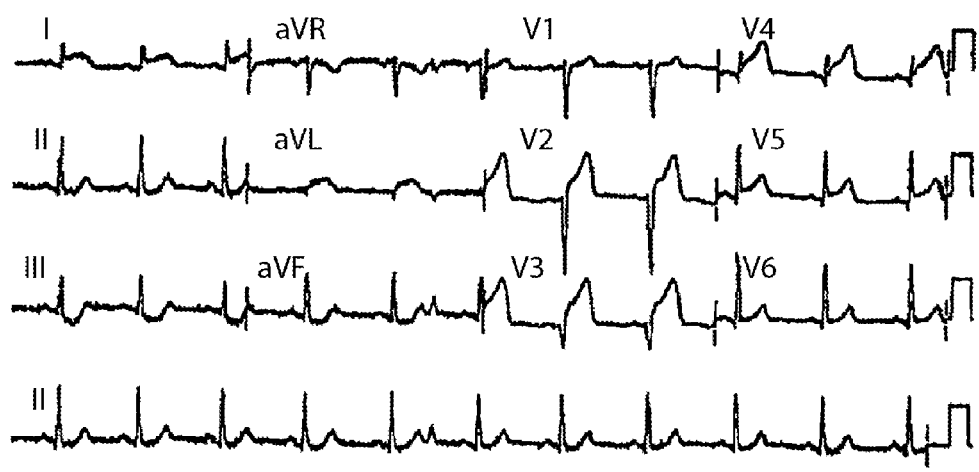

Examples of ECG's are shown in FIGS. 6A-6J. FIG. 6B shows a pattern or ST segment shifts which indicate new infarction, or cell death, in the anterior wall of the heart. (Patient with anterior wall myocardial infarction) The ST segment elevation is most prominent in leads v2 and v3. Notice also the loss of R wave heights compared to the normal ECG of FIG. 6A. That loss of R wave makes it more difficult to gate or trigger imaging by standard methods. In current practice, the imaging technician can spend half an hour or more, trying different lead placements and combinations, seeking a tall R wave for triggering. Note ST elevations in v leads particularly v2, v3, the loss of R waves v2, v3 and the reduced R wave in v4. Standard image gating from any of the standard chest leads v1-v3 would fail to detect the R wave.

Figure 6C:
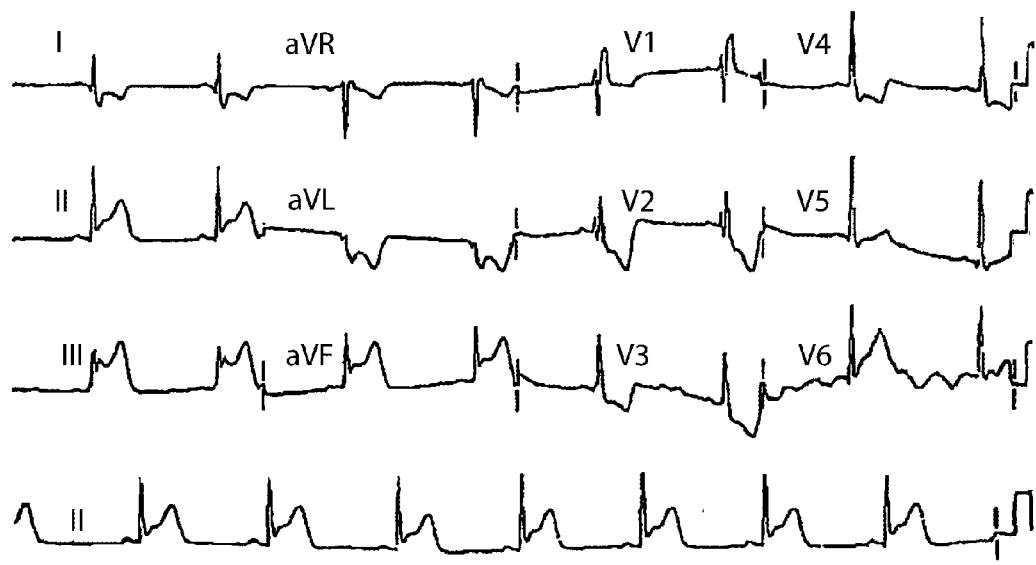

An ST elevation pattern shown in FIG. 6C occurs with inferior wall infarction. (Patient with inferior wall myocardial infarction) Note the ST segment elevations in leads II, III, and aVF. There are reciprocal changes in the ST and T waves of the v leads, but it is vital to examine the former leads or equivalent views to recognize the life-threatening condition. Also, there is a change in the morphology or form of the QRS: a second peak, or R', due to damage in the electrical conduction system in the heart. Such changes commonly interfere with standard ECG trigger methods, as the second peak may trigger instead of the first. Note ST elevations in leads II, III, and aVF, with reciprocal changes in I, aVL, v2-v4. Also note the change in the QRS of v1 and v2 to RSR', evidence of right bundle branch block (abnormality in the electrical activation pathways). It is very important to recognize evidence of acute injury and/or ischemia.

Figure 6D:
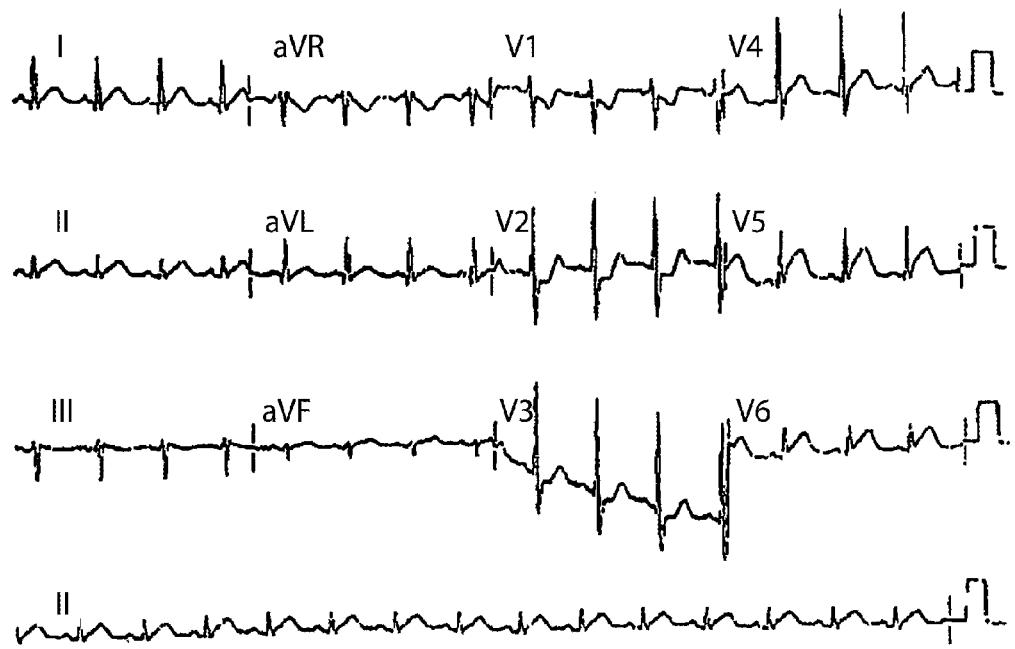

Abnormal Q waves in the posterolateral wall of the heart shown in FIG. 6D indicate an older infarction. (Patient with posterolateral wall myocardial infarction) Note the changes in R wave heights, which could interfere with standard triggering, especially after placement in a magnet (not shown) when the T wave is effectively much taller due to signal from blood in the great vessels moving in a strong magnetic field. Note Q waves in I, aVL, v6 and decreased R wave in II, III, F, v5, v6. Note also baseline drop in v3 which is not helpful in the analysis, and is fully corrected in the present invention.

Figure 6E:
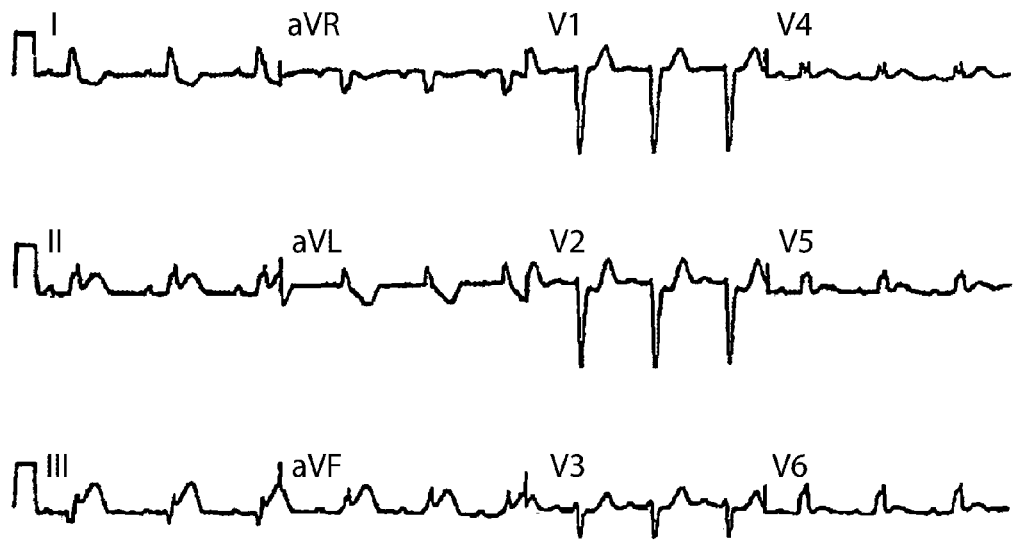

A conduction abnormality as shown in FIG. 6E, not uncommon in patients with heart disease, contradicts the assumption of filtered EKG methods for EKG triggering, that the R wave is narrow. (Patient with left bundle branch block) The pattern shown in FIG. 6E indicates left bundle branch block, resulting in a change in width, height, and form of the QRS. Note the substantive loss of R wave height. With standard systems, it may prove impossible to gate or trigger. Note the wide QRS, and severely reduced R wave in most leads. The usual image gating from any of the standard chest leads v1-v4 would fail to detect the R wave.

Figure 6F:
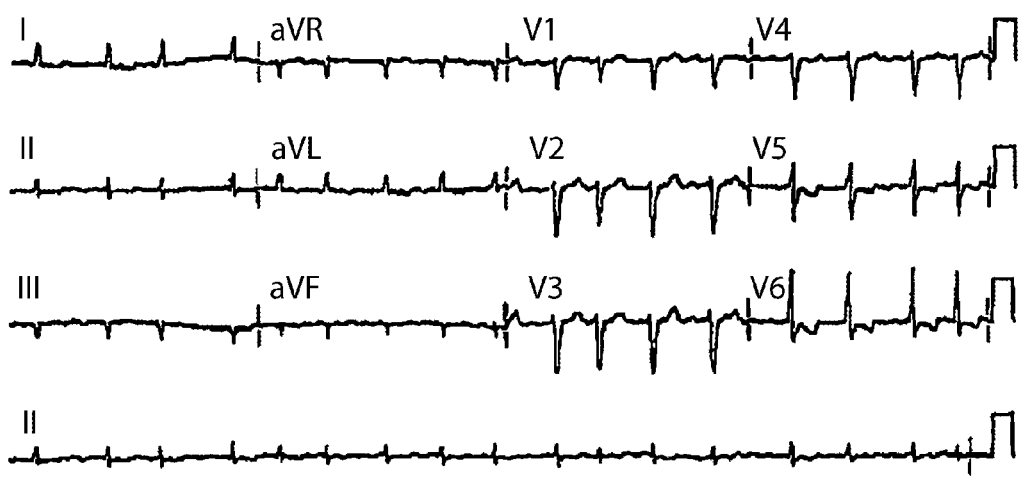

Irregular rhythm due to atrial fibrillation as shown in FIG. 6F also interferes with standard triggering. Standard triggering fails here because the preceding RR interval has very variable length; the amount of time that the ventricle fills with blood varies, the heart size and position varies. (Atrial Fibrillation and Digoxin Effect) The present invention tracks the preceding and average RR interval, so that an imaging system can reject data with long or short filling times, enabling high quality imaging in spite of the arrhythmia. Also, due to variable times of recovery due to varied RR intervals, the R wave may widen as in left bundle branch block. Note the irregular rhythm. Standard image triggering works poorly here because a proper R wave trigger corresponds to variable filling times, and thus different sizes and positions of the heart. Also note changes in the ST segments and T waves related to the medication.

Figure 6G:
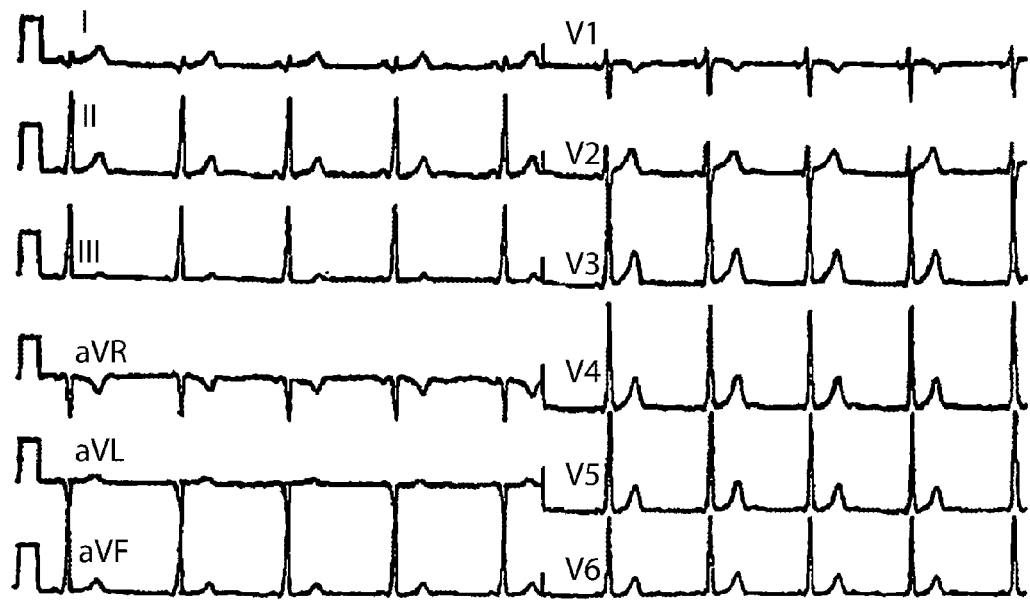

A conduction abnormality from the small chambers to the large chambers as shown in FIG. 6G can result in a short PR interval, and a change in the shape of the QRS: Wolf-Parkinson-White conduction. (Patient with Wolf-Parkinson-White conduction abnormality) This is a congenital condition. The change in shape of the QRS could interfere with systems that rely on narrowness of the R wave as part of the trigger. Note the short interval between the P waves and the R waves and the slurred initiation of the R wave followed by an R wave peak at the normal P-R interval.

Figure 6H:
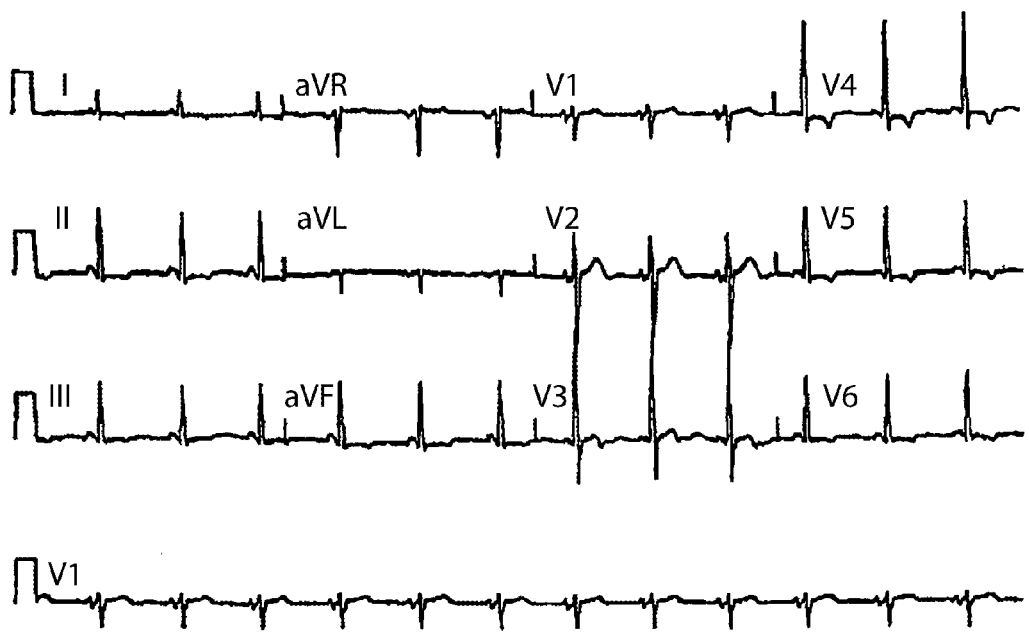

Another conduction abnormality from the small chambers to the large chambers as shown in FIG. 6H that does not change the shape of the QRS is called Lown-Ganong-Levine conduction. (Patient with Lown-Ganong-Levine conduction abnormality) It is helpful to recognize such abnormalities because they are associated with rhythm disturbances, especially under stress. Note the short interval between the P waves and the R waves, without a slurred upstroke.

Figure 6I:
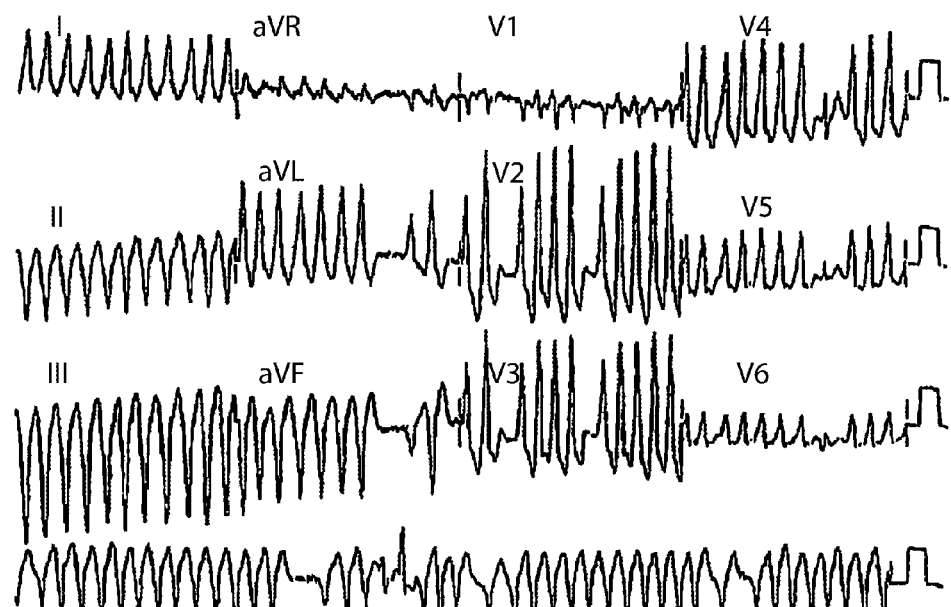

A common rhythm disturbance that may occur with conduction abnormality from the small chambers to the large chambers as shown in FIG. 6I looks similar to a deadly emergency: atrial fibrillation plus Wolf-Parkinson-White conduction. (Patient with Wolf-Parkinson-White syndrome and atrial fibrillation) If the doctors did not note the abnormality before the rhythm change, they might well think this is ventricular tachycardia, a very different potentially life-threatening condition treated by applying a strong electric shock. In standard imaging systems, this might be confused also with gradient switching artifact. The present invention substantively eliminates gradient switching signal, avoiding that potential confusion. Note the rapid irregular timing, esp. in the rhythm strip in the bottom row, and the wide QRS due to the conduction abnormality.

Figure 6J:
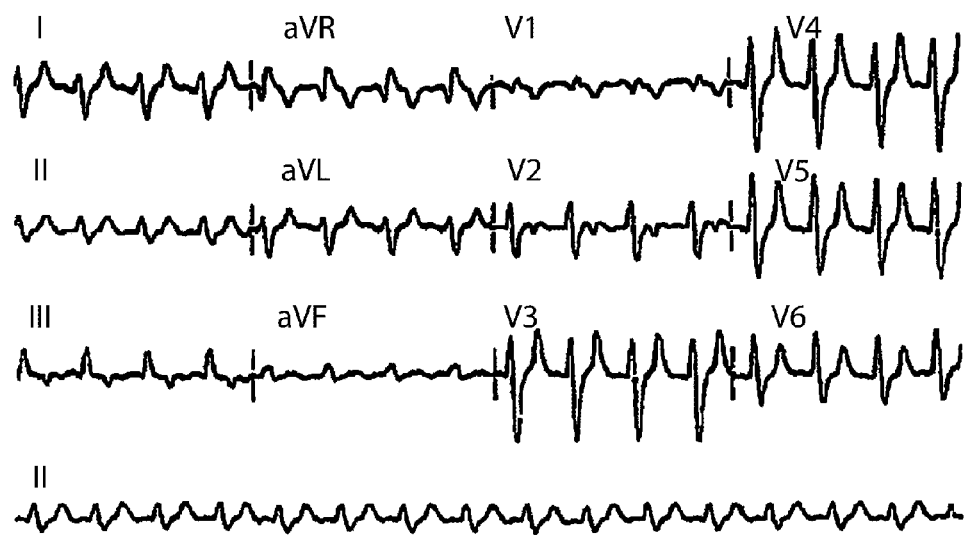

Elevation of potassium level results in tall peaked T waves as shown in FIG. 6J. In standard imaging systems, this could be easily missed, because tall peaked T waves are seen inside magnets routinely, due to signal produced from pulsation of blood in large vessels in the strong magnetic field. High potassium levels can be life threatening. The present invention distinguishes and substantively removes the signal from the magnet, avoiding that potential confusion. Note the tall peaked T waves, which are taller than the R waves in the chest leads v3, v4, I, II, and aVL. A standard image triggering system would trigger off the wrong wave in such circumstance.

Figure 7:
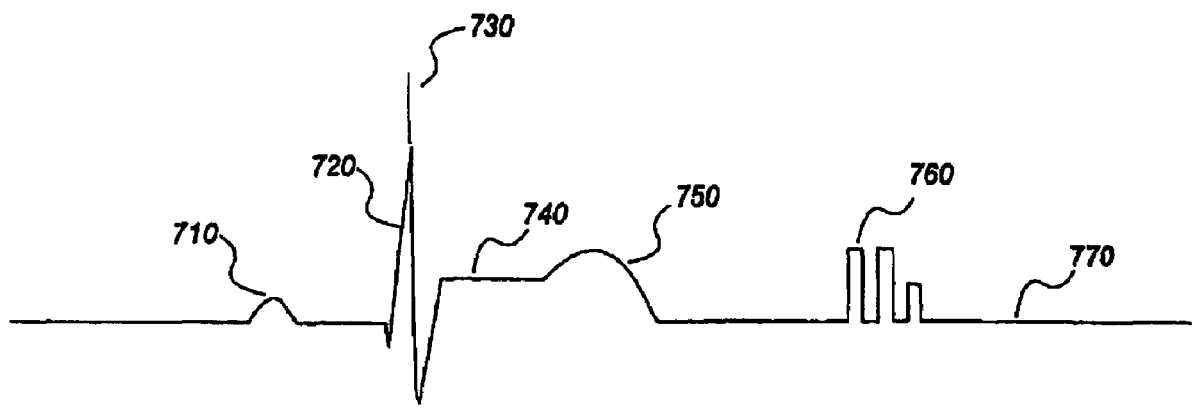
FIG. 7 shows examples of output from the present invention.

An example of synthetic signal from the present invention is illustrated in FIG. 7, which shows a clear P wave 710, QRS 720, pace spike 730, ST segment 740, T wave 750, markers measuring the 2.5 millimeter ST segment elevation 760 and a perfectly flat baseline 770. The synthetic ECG can produce all the standard views, and the extra views that are sometimes important (V7, V8, V9, V4R, and V5R, etc.). Unlike the actual ECG's, the features are even easier to evaluate, because of the flat baseline, substantive elimination of noise, and clear definition of the components. The pace spike 730 does not represent a pacemaker, but rather is a superimposed signal that will trigger legacy imaging systems that simply look for the tallest wave. Optionally, the pace spike will be suppressed by short or long preceding RR intervals, or a separate flag will indicate the occurrence of short or long preceding RR intervals, for effective gating in spite of changes of rhythm. The markers 760 facilitate recognition of significant changes in ST segment height, which will be very important in one of the newer applications of imaging, assessing blood arrival to the heart and/or wall motion or thickening during stress testing.

Figure 8:
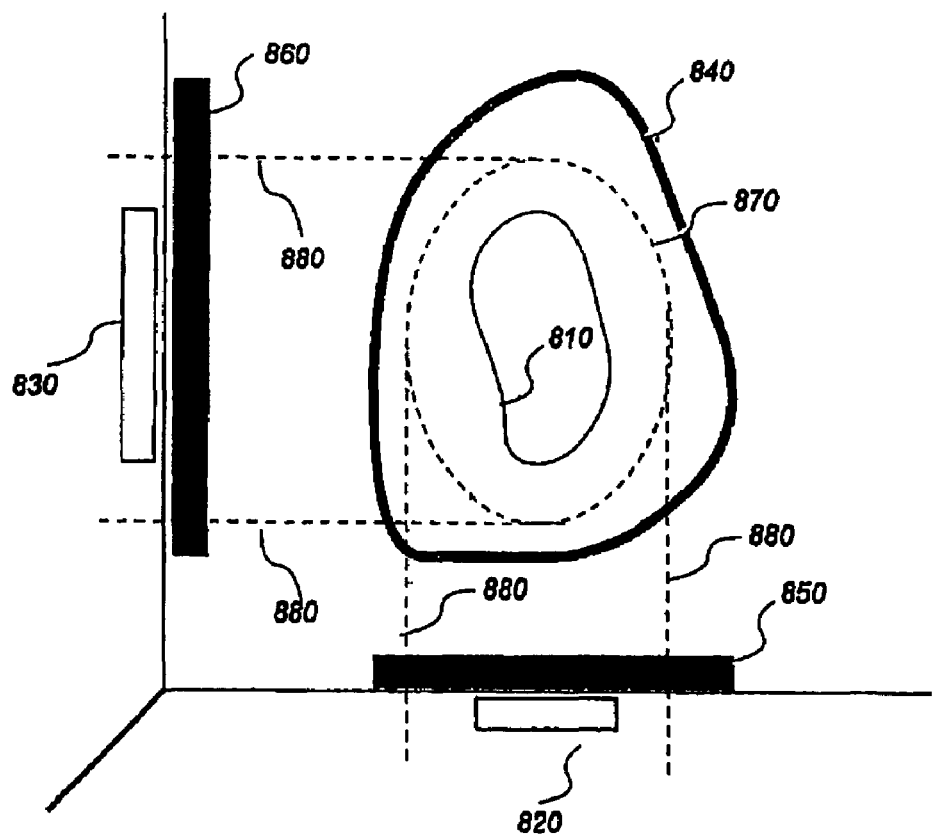
FIG. 8 demonstrates how multivariate signal characterization enables feature extraction where individual variables fail.

A fundamental advantage of the multivariate method of the present invention is illustrated in FIG. 8. For convenience of drawing, the image is on a flat, or two-dimensional region, but is to be understood to represent a region in a plurality of dimensions (distinct coordinates, or data channels), i.e., a multivariate space. The Figure shows a region 810 and another region 840. The hollow bars 820, 830 show the projection of region 810 onto the each of two coordinate axes. The solid bars 850, 860 likewise show the projection of region 840 onto each of two coordinate axes.

The projections correspond to the one-dimensional projections of the electrical activation of the heart that are used for standard ECG leads. Recall that the fact that the heart is not simply an electric dipole means that more than 3 dimensions of data may be required to describe well the electrical activation of the heart; even a standard 12 lead system based on 10 electrodes does not suffice for all subjects.

In neither projection (860 vs. 830, 850 vs. 820), nor in this example, any diagonal projection that could be generated from them, are the projections of the regions 810, 840 separable. The projections overlap substantively. That means the corresponding signals cannot be separated, e.g., by filtering, in the projections. However, in the multivariate space, one can define a border 870 that complete separates 810 from 840. The projections of that border 880 still do not separate the projections of the regions. Such a multivariate border can be easily defined by constraints, based on observing the signal positions from various sources in the multivariate space, for example by taking a one-, or two-, standard-deviation border around the multivariate span of the desired signal, in space-time, static, or as a dynamic border changing throughout the cardiac cycle. We have determined that magnetic field gradient-induced signals, and much of the noise and other artifacts, can be completely separable from the desired signal in multivariate space. Consequently, definition of a multivariate border 870 can separate the signals 810, 840 in multivariate space. Application of the constraints eliminates the unwanted signals.

Exemplary Description of a Training and Use of the System

The following description contemplates separation and recovery of a synthetic EKG signal from superimposed signals acquired ("observed") during magnetic resonance imaging. The present invention, however, is by no means intended to be limited to utilization in such an environment. The present invention allows separation of desired physiologic signals from other signals, and the continuous monitoring of such signals regardless of the presence of an external stimulus (e.g., an MRI magnetic field) As noted above, the template signal is used to train/calibrate a separability operator S that allows the signal components attributable to distinct signal sources that are superimposed in subsequently observed (acquired at the sensors) signals to be separated on multiple channels.

During the training phase, one or more template signals may be selected from: (1) resting multi-lead EKG signals obtained outside the MRI magnet; (2) the aortic pulse form (e.g., the fingertip oximetry waveform that is typically available in MRI); and/or (3) gradient signals (e.g., using signal from the gradient controller or passively detected using loops of wire outside the patient, and/or using the added pathways discussed under EKG monitoring configuration). These signal(s) serve as measures of success for computation of a separability operator S, defined here as a collection of computed coefficients that operate on multivariate data to produce a new view in which superimposed signals are separated.

One more template signals may also be employed concurrently or sequentially. Results are shown below confirming that even a single template (one lead EKG outside the magnet) works quite well to enable untangling of superimposed signals. It is worth repeating here that the existing state of the art in signal separation assumes orthogonal, independent signals. The present invention overcomes that limitation, and enables clean separation of signals from non-orthogonal superimposed signals from multiple sources, e.g., (1) normal 12 lead EKG signals, (2) signals from blood flow (magnetohemodynamic signal), and (3) signals from gradient switching.

Let separability operator S be an m×n matrix of separation operator coefficients, parameters used to recover the desired signals from an obfuscating superposition of observed signals O(t) such as those observed in a magnet (S can also be represented as a vector or as a tensor; the key point is that S represents a plurality of values that specify a model). Here O(t) is an observation vector, a list of values (changing over time), reporting observed values from the multi-lead system. The goal, then, is to compute a result vector, R(t), whose channels better represent the desired signal sources separated from contaminant signals, e.g., $R_1(t)$=EKG v1 signal, as it would appear without superimposed flow signal and/or gradient signals, whereas $O_1(t)$ has contaminating signals, and the different components of O(t) each report different summations of multi-source superimposed signals, in various proportions.

An important factor in the inventive method recognizes that the differences in combining proportions of the multi-source signals varies with the different sensitivities of the individual sensors to the various sources, and this is primarily a reflection of individual differences in subject body form and sensor placement (height, muscle mass distribution, orientation of the heart and great vessels). For example, an electric signal detector overlaying the back of a subject has a slightly stronger contribution of signal from the nearby aorta, and slightly less dominant contribution from the electrical activation of the heart, than another electric signal detector similarly placed but closer to the heart as detected by another lead placed in front of the chest.

This proximity effect is ignored in vector cardiography, which in effect assumes sensors are at "infinity" with differences due only to angulation. In the vector cardiography model, corresponding anterior and posterior detectors would have anterior-posterior signals assumed to add to zero, but that is not a true representation of reality. In fact, a major reason 12-lead EKGs are used clinically, rather than a 3 lead vector cardiogram, is that these near-field effects convey essential information. Individual differences in angulation, lead placement, proximity (near field) effects, and the fact that the cardiac signal is not a point source but rather is a summation from multiple sources, all are accounted for by the present invention.

For concreteness, we consider and illustrate the case where O=(a,p) has just two signal values, one from the front of the chest (a=EKG v1), and one from the back overlaying the aorta (p) as in FIG. 9. The anterior lead (solid disk) is placed at the lower left sternal border near the fifth intercostal space (a), and the corresponding position on the back of the chest gets the second lead (p). These are chest leads, each compared to the "indifferent electrode" reference computed from leads near each of the limbs. The "a" lead is closer to the heart than to the aorta, and the "p" lead is closer to the aorta than to the heart.

Figures 10A, 10B:
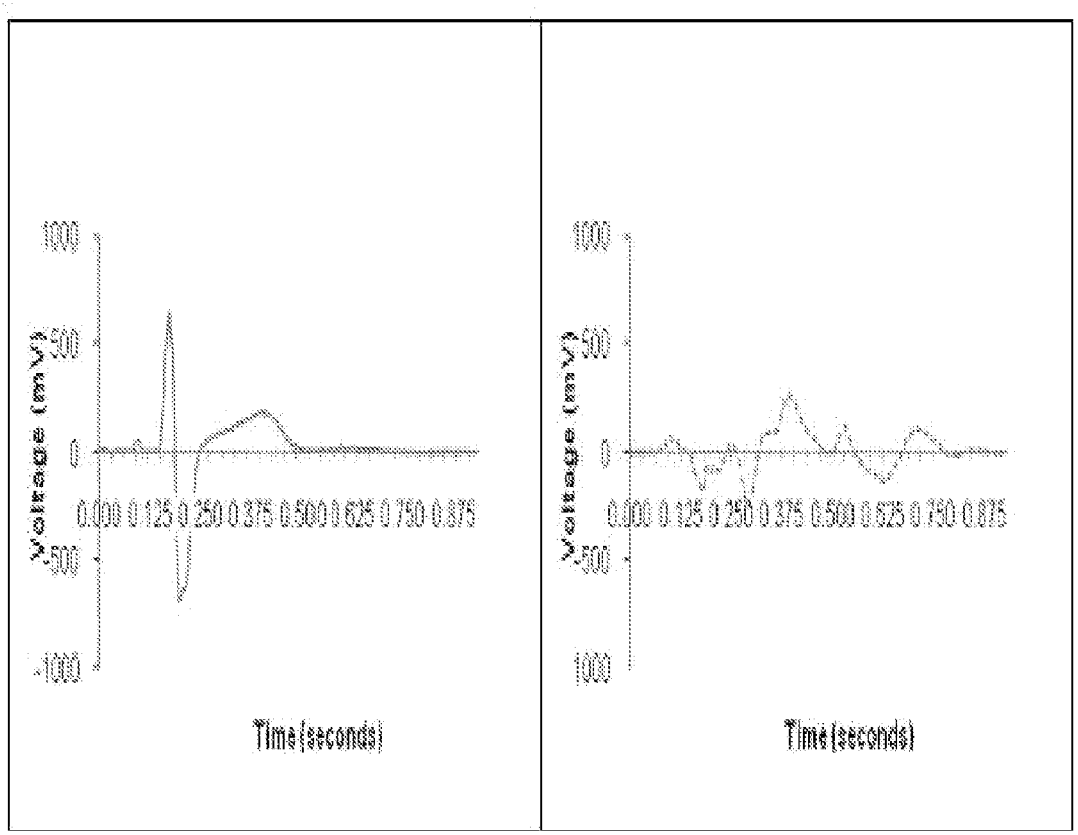
FIGS. 10A and 10B are graphs illustrating two examples of template signals/training data in accordance with an embodiment of the invention.

For the purposes of this example, the actual template data consists of the EKG v1 signal acquired outside of the MRI magnet (such as shown in FIG. 10A) and optionally, the arterial pulse waveform (such as shown in FIG. 10B.) The signal represented in FIG. 10B was computed from combined signals and represents voltages induced by blood movement in the magnet (large veins and arteries, especially the aorta and vena cava) without pulse waveform correction.

Figures 11, 12:
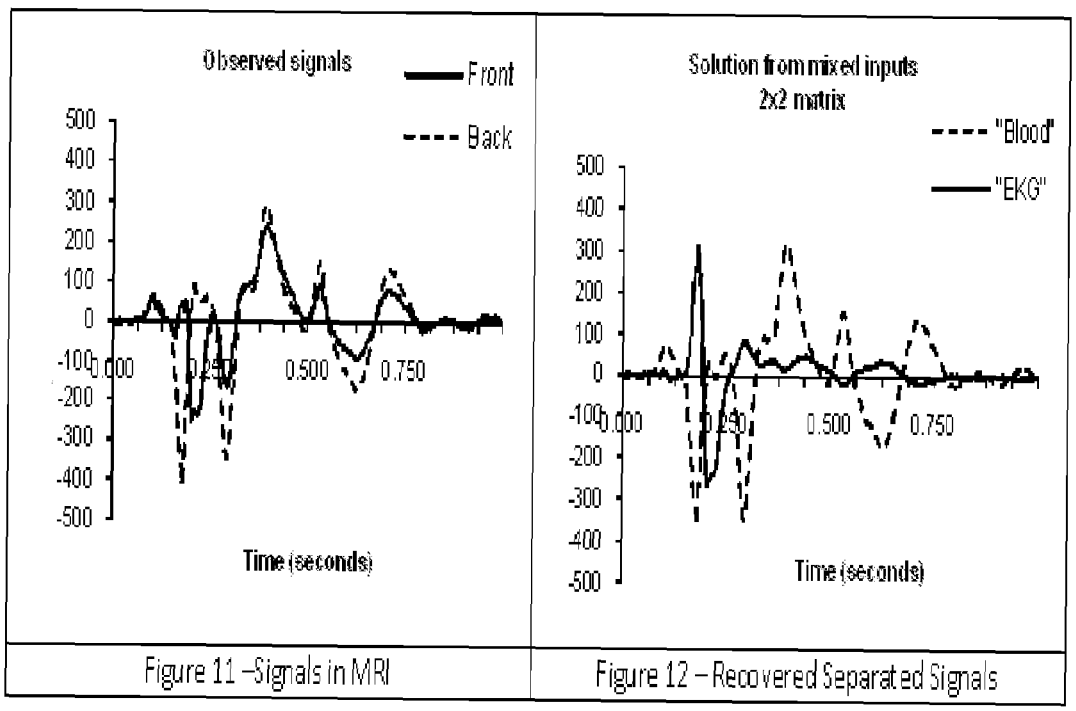
FIG. 11 is a graph representing an example of an observed signal including summed cardiac source signals and vascular source signal components.
FIG. 12 is a graph representing separated (synthetic) signal source components on different channels following the application of a separability operator to the observed signal of FIG. 11.

FIG. 11 shows the signals actually observed, O(t), from the two sensors (one anterior and one posterior to the chest as shown in FIG. 9) employed in this example when inside an MRI imaging magnet. The solid curve O-a represents the sum of cardiac and vascular signals as observed from the anterior chest lead, and the dashed curve O-p represents the slightly different combination observed from the back. Note that O-a appears very different from EKG v1 (FIG. 10A) because O-a is obtained inside the magnet and thus has signal from flow in the great vessels in addition to signal from the heart, whereas EKG v1 was obtained outside the magnet where great vessel flow does not produce any significant signal. Note also that O-b appears similar to O-a, but as it is placed over the back, it has slightly larger influence from the great vessels, and slightly less contribution of signal from the heart, compared to the anterior O-a, due to the fact that signals have different strengths as a function of distance from their source. O-a may be considered, for example, to combine 90% of the cardiac signal source (i.e., the heart) and 70% of the aortic source, while the posterior O-p signal comprises 90% of the aorta signal and 70% of the cardiac signal. The difference in weight of the different sources relates to the fact that contributions are weaker at greater distance.

For this physiologic monitoring arrangement, one can choose separability operator S to be a 2×2 or a 3×3 matrix. First consider $S_{2 \times 2}$ as a matrix with four values, initialized as the identity matrix $$S_{2 \times 2} = \begin{bmatrix} 1 & 0 \\ 0 & 1 \end{bmatrix}.$$

The four components of $S_{2 \times 2}$ relate to the sensitivity of sensor i to signal source j where i represents template signals 1 and 2 (EKG v1, and great vessel flow), and j represents sensors 1 and 2 (at anterior chest and posterior chest positions, respectively); the components of S exploit these different sensitivities to provide signal separation.

The simplest embodiment uses S as a linear operator on the observed signal, $$O(t) = \begin{bmatrix} a(t) \\ p(t) \end{bmatrix},$$

whereby a result vector R(t) is given by:
$$R(t) = S_{2 \times 2} \cdot O(t) = (S_{00}a(t) + S_{01}p(t), S_{10}a(t) + S_{11}p(t)),$$

with the values for $S_{00}$, $S_{01}$, $S_{10}$, and $S_{11}$ determined empirically, tailored to the individual and specific lead placement, based on minimization of an error function. The template signal EKG v1(t) provides the measure of success, by reporting error $$E_1 = \sum_t (R_1(t) - EKGv1(t))^2$$

which is simply a non-negative function that reports closeness of resultant signal to the template, with match at E=0. As in Maximum Likelihood Estimation (the underlying principle for classical statistical tests), this process inverts the role of observation and variable: in the training phase, the values of the operator S matrix are treated as unknowns, while the desired initial result is known (from data obtained outside the magnet). This is similar to modeling a distribution of numbers as having a mean µ and standard deviation σ, treating those numbers as unknowns, and computing the values of µ, σ for which the likelihood of an observed data set is maximized; subsequently µ, σ are treated as known, and new observations are classified in relation to the specified values. Similarly, template data is used to determine values for the operator S matrix, then S may be applied to process subsequently observed signals to separate onto multiple channels the distinct signal source components that are superimposed in the observed signals.

The error function E can be based on just a single template as above, or it can use multiple templates (e.g., compare second channel to the pulse waveform, compare third channel to gradient signals), either separately, or by combining independent error terms into a single summary term $$\left( E = \sum_i E_i, \text{ where } E_i \text{ is error function for component } i \right).$$

FIG. 12 illustrates the separation of the source signals influencing the O-a and O-b signals acquired by the sensors and shown in FIG. 11, after application to O-a and O-b of a 2×2 separability operator S having separation coefficients:

$$\begin{bmatrix} 2.326 & -1.326 \\ 0.500 & 0.500 \end{bmatrix}.$$

These coefficients were computed by minimizing the error between channel one output of R and the EKG v1 template signal observed outside the magnet, then applying the results to new multi-source mixed signal input under same conditions. Thus, the operator S is trained to extract the EKG signal seen outside the MRI by using the sum-square signal difference as the error function; optionally the pulse waveform can be used to estimate the aorta signal (not included is the displayed result), with the squared errors simply summed. The solution may be computed by a Generalized Reduced Gradient (GRG) method.

It is easily demonstrated that application of the separability operator S to serial data thant including changes in the EKG in the form of ST segment deviations produces output in realtime that accurately reflects the ST segment changes, even though they were not part of the training data. This desired behavior is achieved because S is stationary (not a function of time) and reflects geometric aspects of the signal sources without distorting the relation of sequential components to the source waveforms (unlike filters which do distort the waveforms).

Preferred embodiments use additional degrees of freedom to address possible signal offsets such as DC drift. This is made clear by considering the sample example as above, with just two sensors: one anterior, and one posterior, but using a 3×3 matrix instead of 2×2. $S_{3\times3}$ is computed similarly to $S_{2\times2}$ but it supports an additional degree of freedom to accommodate DC offsets in each sensor, and the observation vector O(t) is modified by appending the value 1 to account for the DC offsets. Thus, $R(t)=S\cdot\hat{O}(t)$, where $\hat{O}(t)=\langle O_1(t), O_2(t), \ldots, 1\rangle$. This is analogous to adding an intercept to the equation for a line, rather than just accounting for slope. The benefit of this additional degree of freedom is demonstrated by contaminating the example in FIGS. 10A-10B by adding a DC offset during the training phase. FIG. 13A shows an EKG signal and uncorrected vascular signal distorted by ST elevation (elevated and peaked ST-T wave, solid), plus a DC offset (dashed line). In the presence of a substantial DC offset, the operator $S_{2\times2}$ will distribute the constant offset into the slope terms (the terms specifying sensitivity of sensor i to signal source j). This will impair the fit, resulting in error (FIG. 13C illustrates the distorted result from a 2×2 matrix due to distribution of DC offset into the data channels.)

Using the same single training template EKG v1 to compute values for operator $S_{3\times3}$ one can obtain the results shown in FIG. 13D, with the computed ("synthetic") EKG signal reset to baseline (0 level), and separate DC offset computed (dashed line) as a third channel of output. Note that the ST-T wave is fully recovered. With a change in signal source due to ST elevation, a correct reflection of the signal change (FIG. 13B) may be obtained. FIG. 13B shows the source signals observed in the MRI, from which the accurate, synthetic EKG (FIG. 13D) signal was computed. Further changes in ST T may be monitored in real-time using the computed/trained separability operator S matrix (wherein, as already discussed, the data for solving for the coefficients is obtained from the difference in sensitivity to the different sources, due to proximity.)

Once the approach is selected whereby matrix coefficients of separability operator S are computed so as to minimize error calculated as the difference between channels of output and training data, the actual training calculation is readily accomplished by an iterative solver technique during a brief training phase. Once the coefficients are computed (after training is complete), the operator S can be applied prospectively in real-time to subsequent observed signals O(t) as a short set of add-multiply calculations. At each major iteration for trial solutions during the training phase, an updated search direction is computed by solving, e.g, as a quadratic programming (QP) subproblem. The objective of each QP subproblem is to solve a quadratic approximation of a modified Lagrangian function that depends on the nonlinear problem's objective and constraints which are linear models at the current point of the nonlinear problem's constraints, to identify the direction of vector value change that points towards rapidly reduced error. Even a random direction vector biased to direction change invoked whenever error stops decreasing leads quickly to the desired solution.

For considerably faster training solution, a smooth augmented Lagrangian merit function can be applied with a limited-memory quasi-Newton approximation to the Hessian of the Lagrangian. Its QP subproblems are solved using a reduced-Hessian active-set method, with "elastic programming" techniques to deal with infeasibility in the QP subproblems. For infeasible models, it provides an approximate solution of good practical value. An Interior Point method can be applied called the Homogeneous Self-Dual method. Interior Point or Barrier methods solve a series of barrier subproblems by performing one or more minimization steps on each barrier subproblem, then decreasing a barrier parameter, and repeating the process until the original problem has been solved to desired accuracy.

An Interior Point method uses second derivative information (the Hessian of the Lagrangian of the objective and constraints) at each major iteration but there are several alternatives: One can obtain analytic or estimated first and second derivatives to construct a Hessian approximation using a quasi-Newton (BFGS) or limited-memory quasi-Newton approach; or use analytic or numerically estimated first derivatives to compute approximations of the Hessian-vector products used by the interior point method.

Experiment

Both a hardware embodiment and simulator of the inventive system have been implemented. A clinical test in which 36 pairs of EKGs from a published library of EKGs were analyzed in random order, twice. In each pair, one was a clean EKG obtained outside MRI, and the other was reconstructed from the contaminated/distorted signals representing superposition of the magnetohydrodynamic MRI great vessel signals. An electrophysiology cardiologist (sub-specialist in heart electric signals) found trace or no discernable non-diagnostic differences, no mild or greater non-diagnostic differences, and no diagnostic differences of any severity between recovered signal and the clean EKG signal obtained outside the magnet. The computed signal was actually preferred in 86% of cases, and on the repeat scrambled set of pairs, with different pair order, again the computed signal was preferred in 88% of the cases. When asked to identify the original signal, the computed (synthetic) signal was mistaken for original in 87±1%.

It is to be understood that the above embodiment descriptions are simply illustrative of the principles of the invention. Various and other modifications and changes may be made by those skilled in the art that will embody the principles of the invention and fall within the spirit and scope of the claimed invention.

What is claimed is:

1. A method for determining a condition associated with a live body organ by separating desired physiologic signals produced by the live body organ from superimposed signals acquired during physiologic monitoring via a plurality of physiologic signal sensors at different positions in relation to the live body organ, comprising the steps of:

acquiring multivariate physiologic signals via the plurality signal sensors, wherein the physiologic signals acquired on each of the signal sensors reflects the respective sensitivity of the particular signal sensor to multiple signal sources, including a desired signal and one or more superimposed contaminant signals;

inputting the acquired physiologic signals into a data processor that performs the steps of:

converting the acquired physiologic signals into signal data upon which mathematical operations are performed by representing the acquired signal data as an observation vector O(t) whose values are representative of the physiologic signals acquired by the corresponding sensors;

accessing a separability operator S that includes a matrix of separation coefficients;

applying the separability operator S by dot product to the observation vector O(t) to produce an output;

extracting one or more output signals from the output to determine a condition associated with the live body organ; and enabling the physiological monitoring of the condition associated with the live body organ;

wherein the matrix of separation coefficients collectively specify a model of the conditions of physiologic and external signal sources encountered during data acquisition.

2. The method of claim 1, wherein the live body organ is a heart.

3. The method of claim 1, further comprising training the separability operator S for a particular physiologic monitoring arrangement, through the steps of:

selecting a template signal T(t) associated with a training sensor as a measure of success;

acquiring a new observation O(t) from the training sensor;

initializing the separability operator S to be an i x j matrix, wherein the components of Sixj reflect the sensitivity of the i sensors to j signal sources, where i represents a template signal data coefficient associated with the $i^{th}$ lead, and j represents the particular sensor; redefining the coefficients of S by obtaining a result signal R(t) by dot product of S.O(t), and then adjusting the coefficients of S based on a minimization of an error function calculated as the difference between a channel of the result signal R(t) and the template signal T(t), $$E_1 = \sum_t (R_1(t) - T_1(t))^2.$$

4. The method of claim 3, wherein the template signal T(t) is a resting multi-lead EKG signal.

5. The method of claim 3, wherein
the separability operator S comprises a 2×2 matrix;

$$O(t) = \begin{pmatrix} a(t) \\ p(t) \end{pmatrix}$$

wherein a(t) is the observed signal at an anteriorly positioned sensor, and p(t) is the observed signal at a posteriorly positioned sensor;

the template signal T(t) comprises EKG v1 for the anteriorly positioned sensor, and a signal representing great vessel flow for the posteriorly positioned sensor; and the error function comprises $$E_1 = \sum_t (R_1(t) - EKGv1(t))^2.$$

6. The method of claim 3, wherein:
multiple template signals T(t) are selected; and
the error function comprises a sum of independent error terms, $$E = \sum_i E_i,$$

where $E_i$ is error function for component i.

7. The method of claim 3, further comprising the step of correcting for DC offsets in each sensor through the steps of:

expanding the operator S to support an additional degree of freedom; and appending the value 1 to the observation vector O(t).

8. The method of claim 1, wherein the desired separate physiologic signals represent contributions to overall signal from different regions and the signals from other regions are treated as contaminants with respect to each desired signal.

9. The method of claim 1, wherein the deriving step further comprises the step of:

extracting from the acquired multivariate physiologic signals undesirable signals attributable to distal, global and external signal sources through comparison of the undesirable signals acquired on two or more of the signal channels so as to isolate a local cardiac signal.

10. The method of claim 1, further comprising the step of:
externally generating one or more signals containing information relative to external undesirable signal sources.

11. The method of claim 1, wherein:
each multivariate physiologic signal is coupled to one of the signal sensors by a plurality of electrically conducting leads of similar trajectory not all of which are in electrical contact with the signal sensor, such that a common spurious signal is acquired in each lead attributable to one of the multiple signal sources that is external to the body; and the deriving step further comprises the step of extracting the common signal from the acquired multivariate physiologic signals.

12. The method of claim 1, further comprising the step of:
generating from the output signal a synthetic ECG signal including indications of cardiac electrical activity.

13. A system for determining a condition associated with a live body organ by separating desired physiologic signals produced by the live body organ from superimposed contaminant signals acquired during physiologic monitoring, comprising:

a plurality of sensors adapted to be located at different positions relative to a live body organ for acquiring multivariate physiologic signals, wherein the physiologic signals acquired on each of the sensors reflects the respective sensitivity of the particular signal sensor to multiple signal sources, including a desired signal and one or more superimposed signals;

a separability operator that includes a matrix of separation coefficients;

a data processor in data communication with the plurality of sensors and executing the steps of:

converting the acquired physiologic signals into signal data upon which mathematical operations are performed by representing the acquired signal data as an observation vector O(t) whose values are representative of the physiologic signals acquired by the corresponding sensors;

applying the separability operator S by dot product to the observation vector O(t) to produce an output;

extracting one or more output signals from the output to determine a condition associated with the live body organ; and enabling the physiological monitoring of the condition associated with the live body organ;

wherein the matrix of separation coefficients collectively specify a model of the conditions of physiologic and external signal sources encountered during data acquisition.

14. The system of claim 13, wherein the data processor further executes steps for training the separability operator S for a particular physiologic monitoring arrangement comprising:

selecting a template signal T(t) associated with a training sensor as a measure of success;

acquiring a new observation O(t) from the training sensor;

initializing the separability operator S to be an i x j matrix initialized to the identity matrix, wherein the components of Sixj represent the sensitivity of the i sensors to j signal sources, where i represents a template signal data coefficient associated with the $i^{th}$ lead, and j represents the particular sensor;

redefining the coefficients of S by obtaining a result signal R(t) by dot product of S.O(t), and then adjusting the coefficients of S based on a minimization of an error function calculated as the difference between a channel of the result signal R(t) and the template signal T(t), $$E_1 = \sum_t (R_1(t) - T_1(t))^2.$$

15. The system of claim 14, wherein the template signal T(t) is a resting multi-lead EKG signal.

16. The system of claim 14, wherein:

the separability operator S comprises a 2×2 matrix;

$$O(t) = \begin{bmatrix} a(t) \\ p(t) \end{bmatrix},$$

wherein a(t) is the observed signal at an anteriorly positioned sensor, and p(t) is the observed signal at a posteriorly positioned sensor;

the template signal T(t) comprises EKG v1 for the anteriorly positioned sensor, and a signal representing great vessel flow for the posteriorly positioned sensor; and the error function comprises $$E_1 = \sum_t (R_1(t) - EKG\,v1(t))^2.$$

17. The system of claim 14, wherein:

the data processor executes a step of selecting multiple template signals T(t); and the error function comprises a sum of independent error terms, $$E = \sum_i E_i,$$

where $E_i$ is error function for component i.

18. The system pf claim 14, wherein the data processor executes steps correcting for DC offsets in each sensor comprising:

expanding the operator S to support an additional degree of freedom; and appending the value 1 to the observation vector O(t).

* * * * *